United States Patent
Flower et al.

(10) Patent No.: US 10,631,746 B2
(45) Date of Patent: Apr. 28, 2020

(54) QUANTIFICATION OF ABSOLUTE BLOOD FLOW IN TISSUE USING FLUORESCENCE-MEDIATED PHOTOPLETHYSMOGRAPHY

(71) Applicant: Novadaq Technologies ULC, Burnaby (CA)

(72) Inventors: Robert W. Flower, Hunt Valley, MD (US); Robert Anthony Stead, Vancouver (CA); Arthur E. Bailey, North Vancouver (CA)

(73) Assignee: Novadaq Technologies ULC, Burnaby (CA)

( * ) Notice: Subject to any disclaimer, the term of this patent is extended or adjusted under 35 U.S.C. 154(b) by 299 days.

(21) Appl. No.: 15/517,895

(22) PCT Filed: Oct. 9, 2014

(86) PCT No.: PCT/IB2014/065189
§ 371 (c)(1),
(2) Date: Apr. 7, 2017

(87) PCT Pub. No.: WO2016/055837
PCT Pub. Date: Apr. 14, 2016

(65) Prior Publication Data
US 2017/0303800 A1    Oct. 26, 2017

(51) Int. Cl.
*A61B 5/026*    (2006.01)
*A61B 5/0275*    (2006.01)
(Continued)

(52) U.S. Cl.
CPC .......... *A61B 5/0261* (2013.01); *A61B 5/0071* (2013.01); *A61B 5/0275* (2013.01);
(Continued)

(58) Field of Classification Search
CPC combination set(s) only.
See application file for complete search history.

(56) References Cited

U.S. PATENT DOCUMENTS

| 4,109,647 A | 8/1978 | Stern et al. |
| 4,162,405 A | 7/1979 | Chance et al. |

(Continued)

FOREIGN PATENT DOCUMENTS

| AT | 409451 B | 8/2002 |
| CA | 2212257 A1 | 8/1996 |

(Continued)

OTHER PUBLICATIONS

Akintunde, A. et al. (Oct.-Nov. 1992). "Quadruple Labeling of Brain-Stem Neurons: A Multiple Retrograde Fluorescent Tracer Study of Axonal Collateralization," *Journal of Neuroscience* Methods 45(1-2):15-22.

(Continued)

*Primary Examiner* — Sean P Dougherty
(74) *Attorney, Agent, or Firm* — Morrison & Foerster LLP

(57) ABSTRACT

A method, an apparatus, and a kit including the apparatus and a fluorescence agent are provided for measuring a time-varying change in an amount of blood in a tissue volume, and include exciting a fluorescence agent in the blood, acquiring a time-varying light intensity signal during a pulsatile flow of the blood through the tissue volume, the pulsatile flow having a systolic and a diastolic phase resembling a conventional photoplethysmogram, and processing the acquired signal by applying a modified Beer-Lambert law to obtain a measurement of the time-varying change in the amount of blood in the tissue volume. The instantaneous molar concentration of the fluorescence agent is determined by utilizing a concentration-mediated change in a fluorescence emission spectrum of the fluorescence agent. There is further provided a fluorescence agent for use in the method.

17 Claims, 10 Drawing Sheets

(51) Int. Cl.
*A61B 5/00* (2006.01)
*A61B 5/0295* (2006.01)

(52) U.S. Cl.
CPC .............. *A61B 5/0295* (2013.01); *A61B 5/00* (2013.01); *A61B 5/6826* (2013.01)

(56) References Cited

U.S. PATENT DOCUMENTS

| | | |
|---|---|---|
| 4,200,801 A | 4/1980 | Schuresko |
| 4,263,916 A | 4/1981 | Brooks et al. |
| 4,394,199 A | 7/1983 | Barnhard, IV et al. |
| 4,473,841 A | 9/1984 | Murakoshi et al. |
| 4,532,918 A | 8/1985 | Wheeler |
| 4,541,438 A | 9/1985 | Parker et al. |
| 4,556,057 A | 12/1985 | Hiruma et al. |
| 4,619,249 A | 10/1986 | Landry |
| 4,718,417 A | 1/1988 | Kittrell et al. |
| 4,719,508 A | 1/1988 | Sasaki et al. |
| 4,768,513 A | 9/1988 | Suzuki |
| 4,773,097 A | 9/1988 | Suzaki et al. |
| 4,774,568 A | 9/1988 | Matsuo |
| 4,786,813 A | 11/1988 | Svanberg et al. |
| 4,805,597 A | 2/1989 | Iwakoshi |
| 4,815,848 A | 3/1989 | Hadeishi |
| 4,821,117 A | 4/1989 | Sekiguchi |
| 4,827,908 A | 5/1989 | Matsuo |
| 4,852,579 A | 8/1989 | Gilstad et al. |
| 4,858,001 A | 8/1989 | Milbank et al. |
| 4,860,731 A | 8/1989 | Matsuura |
| 4,867,137 A | 9/1989 | Takahashi |
| 4,868,647 A | 9/1989 | Uehara et al. |
| 4,900,934 A | 2/1990 | Peeters et al. |
| 4,930,516 A | 6/1990 | Alfano et al. |
| 4,938,205 A | 6/1990 | Nudelman |
| 4,957,114 A | 9/1990 | Zeng et al. |
| 4,993,404 A | 2/1991 | Lane |
| 4,995,396 A | 2/1991 | Inaba et al. |
| 4,995,398 A | 2/1991 | Turnidge |
| 4,998,972 A | 3/1991 | Chin et al. |
| 5,003,977 A | 4/1991 | Suzuki et al. |
| 5,042,494 A | 8/1991 | Alfano |
| 5,071,417 A | 12/1991 | Sinofsky |
| 5,078,150 A | 1/1992 | Hara et al. |
| 5,090,400 A | 2/1992 | Saito |
| 5,091,652 A | 2/1992 | Mathies et al. |
| 5,115,137 A | 5/1992 | Andersson-Engels et al. |
| 5,117,466 A | 5/1992 | Buican et al. |
| 5,125,404 A | 6/1992 | Kittrell et al. |
| 5,131,398 A | 7/1992 | Alfano et al. |
| 5,134,662 A | 7/1992 | Bacus et al. |
| 5,150,292 A | 9/1992 | Hoffmann et al. |
| 5,165,079 A | 11/1992 | Schulz-Hennig |
| 5,178,616 A | 1/1993 | Uemiya et al. |
| 5,196,928 A | 3/1993 | Karasawa et al. |
| 5,214,503 A | 5/1993 | Chiu et al. |
| 5,225,883 A | 7/1993 | Carter et al. |
| 5,255,087 A | 10/1993 | Nakamura et al. |
| 5,279,298 A | 1/1994 | Flower |
| 5,318,023 A | 6/1994 | Vari et al. |
| 5,318,024 A | 6/1994 | Kittrell et al. |
| 5,318,869 A | 6/1994 | Hashimoto et al. |
| 5,340,592 A | 8/1994 | Goodrich, Jr. et al. |
| 5,361,769 A | 11/1994 | Nilsson |
| 5,365,057 A | 11/1994 | Morley et al. |
| 5,371,355 A | 12/1994 | Wodecki |
| 5,375,603 A | 12/1994 | Feiler |
| 5,377,676 A | 1/1995 | Vari et al. |
| 5,377,686 A | 1/1995 | O'Rourke et al. |
| 5,394,199 A | 2/1995 | Flower |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,421,339 A | 6/1995 | Ramanujam et al. |
| 5,424,841 A | 6/1995 | Van Gelder et al. |
| 5,430,476 A | 7/1995 | Häfele et al. |
| 5,437,274 A | 8/1995 | Khoobehi et al. |
| 5,438,989 A | 8/1995 | Hochman et al. |
| 5,453,448 A | 9/1995 | Narciso, Jr. |
| 5,465,718 A | 11/1995 | Hochman et al. |
| 5,491,343 A | 2/1996 | Brooker |
| 5,496,369 A | 3/1996 | Howard, III |
| 5,507,287 A | 4/1996 | Palcic et al. |
| 5,514,127 A | 5/1996 | Shanks |
| 5,519,534 A | 5/1996 | Smith et al. |
| 5,576,013 A | 11/1996 | Williams et al. |
| 5,590,660 A | 1/1997 | MacAulay et al. |
| 5,623,930 A | 4/1997 | Wright et al. |
| 5,627,907 A | 5/1997 | Gur et al. |
| 5,647,368 A | 7/1997 | Zeng et al. |
| 5,656,498 A | 8/1997 | Iijima et al. |
| 5,662,644 A | 9/1997 | Swor |
| 5,664,574 A | 9/1997 | Chance |
| 5,673,701 A | 10/1997 | Chance |
| 5,689,241 A | 11/1997 | Clarke, Sr. et al. |
| 5,699,798 A | 12/1997 | Hochman et al. |
| 5,707,986 A | 1/1998 | Miller et al. |
| 5,732,707 A | 3/1998 | Widder et al. |
| 5,741,648 A | 4/1998 | Hemstreet, III et al. |
| 5,743,266 A | 4/1998 | Levene et al. |
| 5,756,541 A | 5/1998 | Strong et al. |
| 5,785,965 A | 7/1998 | Pratt et al. |
| 5,803,914 A | 9/1998 | Ryals et al. |
| 5,827,190 A | 10/1998 | Palcic et al. |
| 5,845,639 A | 12/1998 | Hochman et al. |
| 5,851,181 A | 12/1998 | Talmor |
| 5,865,754 A | 2/1999 | Sevick-Muraca et al. |
| 5,910,510 A | 6/1999 | Strong et al. |
| 5,919,616 A | 7/1999 | Aurelian et al. |
| 5,927,284 A | 7/1999 | Borst et al. |
| 5,935,942 A | 8/1999 | Zeimer |
| 5,951,980 A | 9/1999 | Cohen |
| 5,956,435 A | 9/1999 | Buzug et al. |
| 5,965,356 A | 10/1999 | Aurelian et al. |
| 5,999,841 A | 12/1999 | Aoyagi et al. |
| 6,008,889 A | 12/1999 | Zeng et al. |
| 6,013,265 A | 1/2000 | Aurelian |
| 6,021,344 A | 2/2000 | Lui et al. |
| 6,032,070 A | 2/2000 | Flock et al. |
| 6,054,131 A | 4/2000 | Aurelian |
| 6,069,689 A | 5/2000 | Zeng et al. |
| 6,074,627 A | 6/2000 | Dean et al. |
| 6,081,612 A | 6/2000 | Gutkowicz-Krusin et al. |
| 6,093,149 A | 7/2000 | Guracar et al. |
| 6,122,042 A | 9/2000 | Wunderman et al. |
| 6,140,314 A | 10/2000 | Zeimer |
| 6,148,227 A | 11/2000 | Wagnières et al. |
| 6,149,671 A | 11/2000 | Nordquist et al. |
| 6,162,242 A | 12/2000 | Peyman |
| 6,178,340 B1 | 1/2001 | Svetliza |
| 6,179,421 B1 | 1/2001 | Pang |
| 6,186,628 B1 | 2/2001 | Van de Velde |
| 6,196,226 B1 | 3/2001 | Hochman et al. |
| 6,207,168 B1 | 3/2001 | Aurelian |
| 6,211,953 B1 | 4/2001 | Niino et al. |
| 6,217,848 B1 | 4/2001 | Achilefu et al. |
| 6,223,069 B1 | 4/2001 | Pfeiffer et al. |
| 6,233,480 B1 | 5/2001 | Hochman et al. |
| 6,241,672 B1 | 6/2001 | Hochman et al. |
| 6,246,901 B1 | 6/2001 | Benaron |
| 6,248,727 B1 | 6/2001 | Zeimer |
| 6,263,227 B1 | 7/2001 | Boggett et al. |
| 6,272,374 B1 | 8/2001 | Flock et al. |
| 6,280,386 B1 | 8/2001 | Alfano et al. |
| 6,293,911 B1 | 9/2001 | Imasizumi et al. |
| 6,319,273 B1 | 11/2001 | Cheen et al. |
| 6,331,703 B1 | 12/2001 | Yarnall et al. |
| 6,335,429 B1 | 1/2002 | Cai et al. |
| 6,351,663 B1 | 2/2002 | Flower et al. |
| 6,351,667 B1 | 2/2002 | Godie |
| 6,353,750 B1 | 3/2002 | Kimura et al. |
| 6,399,354 B1 | 6/2002 | Knipe et al. |
| 6,440,950 B1 | 8/2002 | Zeimer |
| 6,443,976 B1 | 9/2002 | Flower et al. |
| 6,447,443 B1 | 9/2002 | Keogh et al. |

(56) References Cited

U.S. PATENT DOCUMENTS

| | | | |
|---|---|---|---|
| 6,485,413 B1 | 11/2002 | Boppart et al. | |
| 6,498,945 B1 | 12/2002 | Alfheim et al. | |
| 6,544,183 B2 | 4/2003 | Thorn Leeson et al. | |
| 6,566,641 B1 | 5/2003 | Suda | |
| 6,577,884 B1* | 6/2003 | Boas | A61B 5/0073 |
| | | | 600/310 |
| 6,603,552 B1 | 8/2003 | Cline et al. | |
| 6,621,917 B1 | 9/2003 | Vilser | |
| 6,631,286 B2 | 10/2003 | Pfeiffer et al. | |
| 6,671,540 B1 | 12/2003 | Hochman | |
| 6,757,554 B2 | 6/2004 | Rubinstein et al. | |
| 6,804,549 B2 | 10/2004 | Hayashi | |
| 6,821,946 B2 | 11/2004 | Goldspink et al. | |
| 6,840,933 B1 | 1/2005 | Pang et al. | |
| 6,853,857 B2 | 2/2005 | Pfeiffer et al. | |
| 6,882,366 B1 | 4/2005 | Kijima et al. | |
| 6,899,675 B2 | 5/2005 | Cline et al. | |
| 6,915,154 B1 | 7/2005 | Docherty et al. | |
| 6,936,043 B2 | 8/2005 | Peyman | |
| 6,944,493 B2 | 9/2005 | Alam et al. | |
| 7,113,817 B1 | 9/2006 | Winchester, Jr. et al. | |
| 7,236,815 B2 | 6/2007 | Richards-Kortum et al. | |
| 7,317,554 B2 | 1/2008 | Ueda et al. | |
| 7,364,574 B2 | 4/2008 | Flower | |
| 7,381,400 B2 | 6/2008 | Woltering | |
| 7,400,753 B2 | 7/2008 | Seino et al. | |
| 7,400,755 B2 | 7/2008 | West et al. | |
| 7,474,906 B2* | 1/2009 | Rubinstein | A61B 5/0059 |
| | | | 600/317 |
| 7,482,318 B2 | 1/2009 | Aurelian et al. | |
| 7,581,191 B2 | 8/2009 | Rice et al. | |
| 7,729,750 B2 | 6/2010 | Tromberg et al. | |
| 7,774,048 B2 | 8/2010 | Nakaoka et al. | |
| 7,881,777 B2 | 2/2011 | Docherty et al. | |
| 7,885,438 B2 | 2/2011 | Uppaluri et al. | |
| 8,036,437 B2 | 10/2011 | Arditi et al. | |
| 8,073,224 B2 | 12/2011 | Strobel et al. | |
| 8,144,958 B2 | 3/2012 | Nahm et al. | |
| 8,185,176 B2 | 5/2012 | Mangat et al. | |
| 8,194,981 B2 | 6/2012 | Suzuki | |
| 8,285,353 B2* | 10/2012 | Choi | A61B 5/0059 |
| | | | 600/310 |
| 8,361,775 B2 | 1/2013 | Flower | |
| 8,406,860 B2 | 3/2013 | Dvorsky et al. | |
| 8,480,579 B2 | 7/2013 | Serov et al. | |
| 8,521,260 B2 | 8/2013 | Grinvald et al. | |
| 8,538,107 B2 | 9/2013 | Röttger | |
| 8,647,605 B2 | 2/2014 | Mangat et al. | |
| 8,718,747 B2* | 5/2014 | Bjornerud | A61B 5/055 |
| | | | 382/128 |
| 8,725,225 B2 | 5/2014 | Golijanin et al. | |
| 8,892,190 B2 | 11/2014 | Docherty et al. | |
| 8,929,974 B2 | 1/2015 | Hauger et al. | |
| 8,965,488 B2 | 2/2015 | Dvorsky et al. | |
| 9,089,601 B2 | 7/2015 | Golijanin et al. | |
| 9,129,366 B2 | 9/2015 | Nahm et al. | |
| 9,241,636 B2 | 1/2016 | Koizumi et al. | |
| RE45,916 E | 3/2016 | Golijanin et al. | |
| 9,351,644 B2 | 5/2016 | Nahm et al. | |
| 9,357,931 B2 | 6/2016 | Nahm et al. | |
| 9,421,280 B2 | 8/2016 | Mangat et al. | |
| 9,451,903 B2* | 9/2016 | Feinberg | A61B 5/055 |
| 9,554,738 B1* | 1/2017 | Gulati | A61B 5/1455 |
| 9,610,021 B2 | 4/2017 | Dvorsky et al. | |
| 9,642,532 B2 | 5/2017 | Fengler et al. | |
| 9,816,930 B2 | 11/2017 | Moriyama et al. | |
| 9,936,887 B2 | 4/2018 | Dvorsky et al. | |
| 10,041,042 B2 | 8/2018 | Flower | |
| 10,219,742 B2 | 3/2019 | Dvorsky et al. | |
| 10,231,624 B2 | 3/2019 | Mangat et al. | |
| 10,265,419 B2 | 4/2019 | Golijanin | |
| 10,278,585 B2 | 5/2019 | Ferguson, Jr. et al. | |
| 10,285,603 B2* | 5/2019 | Flower | A61B 5/0275 |
| 2002/0007123 A1* | 1/2002 | Balas | A61B 1/303 |
| | | | 600/476 |
| 2002/0025541 A1 | 2/2002 | Nelson et al. | |
| 2002/0038120 A1 | 3/2002 | Duhaylongsod et al. | |
| 2002/0049389 A1* | 4/2002 | Abreu | A61B 3/1241 |
| | | | 600/558 |
| 2002/0099279 A1 | 7/2002 | Pfeiffer et al. | |
| 2002/0099295 A1 | 7/2002 | Gil et al. | |
| 2002/0146369 A1 | 10/2002 | Goldenberg | |
| 2002/0181752 A1 | 12/2002 | Wallo et al. | |
| 2002/0183621 A1 | 12/2002 | Pfeiffer et al. | |
| 2003/0032885 A1 | 2/2003 | Rubinstein et al. | |
| 2003/0050543 A1 | 3/2003 | Hartmann | |
| 2003/0060718 A1 | 3/2003 | Alam et al. | |
| 2003/0060722 A1 | 3/2003 | Pfeiffer et al. | |
| 2003/0064025 A1 | 4/2003 | Yang et al. | |
| 2003/0093064 A1 | 5/2003 | Peyman | |
| 2003/0093065 A1 | 5/2003 | Peyman | |
| 2003/0127609 A1* | 7/2003 | El-Hage | G01N 21/253 |
| | | | 250/574 |
| 2003/0139667 A1* | 7/2003 | Hewko | A61B 5/0059 |
| | | | 600/410 |
| 2003/0156252 A1 | 8/2003 | Morris et al. | |
| 2003/0187349 A1 | 10/2003 | Kaneko et al. | |
| 2003/0232016 A1 | 12/2003 | Heinrich | |
| 2003/0236458 A1 | 12/2003 | Hochman | |
| 2004/0002660 A1 | 1/2004 | Mielekamp | |
| 2004/0066961 A1 | 4/2004 | Spreeuwers et al. | |
| 2004/0077952 A1 | 4/2004 | Rafter et al. | |
| 2004/0109231 A1 | 6/2004 | Haisch et al. | |
| 2004/0156782 A1 | 8/2004 | Alam et al. | |
| 2004/0162489 A1 | 8/2004 | Richards-Kortum et al. | |
| 2004/0171827 A1 | 9/2004 | Peng et al. | |
| 2004/0174495 A1 | 9/2004 | Levine | |
| 2005/0019744 A1 | 1/2005 | Bertuglia | |
| 2005/0020891 A1 | 1/2005 | Rubinstein et al. | |
| 2005/0033145 A1 | 2/2005 | Graham et al. | |
| 2005/0065432 A1* | 3/2005 | Kimura | A61B 5/0263 |
| | | | 600/420 |
| 2005/0069525 A1 | 3/2005 | Mikael | |
| 2005/0089866 A1 | 4/2005 | Hinuma et al. | |
| 2005/0107380 A1 | 5/2005 | Nimmo et al. | |
| 2005/0142556 A1 | 6/2005 | Hoon et al. | |
| 2005/0182321 A1 | 8/2005 | Frangioni | |
| 2005/0182327 A1 | 8/2005 | Petty et al. | |
| 2005/0182431 A1 | 8/2005 | Hausen et al. | |
| 2005/0182434 A1 | 8/2005 | Docherty et al. | |
| 2005/0187477 A1 | 8/2005 | Serov et al. | |
| 2005/0197583 A1 | 9/2005 | Chance | |
| 2005/0254008 A1 | 11/2005 | Ferguson et al. | |
| 2006/0011853 A1* | 1/2006 | Spartiotis | H01L 27/14634 |
| | | | 250/370.13 |
| 2006/0013768 A1 | 1/2006 | Woltering | |
| 2006/0079750 A1 | 4/2006 | Fauci et al. | |
| 2006/0108509 A1 | 5/2006 | Frangioni et al. | |
| 2006/0118742 A1 | 6/2006 | Levenson et al. | |
| 2006/0147897 A1 | 7/2006 | Grinvald et al. | |
| 2006/0239921 A1 | 10/2006 | Mangat et al. | |
| 2006/0241499 A1 | 10/2006 | Irion et al. | |
| 2007/0121099 A1 | 5/2007 | Matsumoto et al. | |
| 2007/0122344 A1 | 5/2007 | Golijanin | |
| 2007/0122345 A1 | 5/2007 | Golijanin | |
| 2007/0203413 A1 | 8/2007 | Frangioni | |
| 2007/0254276 A1 | 11/2007 | Deutsch et al. | |
| 2008/0007733 A1 | 1/2008 | Marks et al. | |
| 2008/0015446 A1 | 1/2008 | Mahmood et al. | |
| 2008/0025918 A1 | 1/2008 | Frangioni et al. | |
| 2008/0044073 A1 | 2/2008 | Bernhardt et al. | |
| 2008/0081990 A1 | 4/2008 | Berenfeld et al. | |
| 2008/0161744 A1 | 7/2008 | Golijanin et al. | |
| 2008/0188728 A1* | 8/2008 | Neumann | A61B 5/02416 |
| | | | 600/336 |
| 2008/0221421 A1* | 9/2008 | Choi | A61B 5/0261 |
| | | | 600/363 |
| 2008/0221648 A1 | 9/2008 | Flower | |
| 2008/0239070 A1 | 10/2008 | Westwick et al. | |
| 2008/0319309 A1 | 12/2008 | Bredno et al. | |
| 2009/0005693 A1 | 1/2009 | Brauner et al. | |

(56) References Cited

U.S. PATENT DOCUMENTS

| | | |
|---|---|---|
| 2009/0042179 A1 | 2/2009 | Peltie et al. |
| 2009/0048516 A1 | 2/2009 | Yoshikawa et al. |
| 2009/0054788 A1 | 2/2009 | Hauger et al. |
| 2009/0112097 A1* | 4/2009 | Kato ............... A61B 8/461 600/458 |
| 2009/0118623 A1 | 5/2009 | Serov et al. |
| 2009/0137902 A1 | 5/2009 | Frangioni et al. |
| 2009/0252682 A1 | 10/2009 | Hillman |
| 2009/0297004 A1 | 12/2009 | Baumgart |
| 2010/0016669 A1 | 1/2010 | Takaoka et al. |
| 2010/0022898 A1 | 1/2010 | Rubinstein et al. |
| 2010/0036217 A1 | 2/2010 | Choi et al. |
| 2010/0041999 A1 | 2/2010 | Schuhrke et al. |
| 2010/0061604 A1 | 3/2010 | Nahm et al. |
| 2010/0069759 A1 | 3/2010 | Schuhrke et al. |
| 2010/0080757 A1* | 4/2010 | Haaga ............ A61B 5/0263 424/9.3 |
| 2010/0099961 A1 | 4/2010 | Hubner et al. |
| 2010/0222673 A1 | 9/2010 | Mangat et al. |
| 2010/0286529 A1 | 11/2010 | Carroll et al. |
| 2011/0001061 A1 | 1/2011 | Ishihara |
| 2011/0013002 A1 | 1/2011 | Thompson et al. |
| 2011/0063427 A1 | 3/2011 | Fengler et al. |
| 2011/0071403 A1 | 3/2011 | Sevick-Muraca et al. |
| 2011/0098685 A1 | 4/2011 | Flower |
| 2011/0306877 A1 | 12/2011 | Dvorsky et al. |
| 2012/0026325 A1 | 2/2012 | Bunker et al. |
| 2012/0078093 A1 | 3/2012 | Flower |
| 2012/0252699 A1 | 4/2012 | Jaffrey et al. |
| 2012/0165627 A1 | 6/2012 | Yamamoto |
| 2012/0165662 A1 | 6/2012 | Nahm et al. |
| 2012/0271176 A1 | 10/2012 | Moghaddam et al. |
| 2012/0323118 A1* | 12/2012 | Menon Gopalakrishna ................ A61B 6/463 600/431 |
| 2013/0035569 A1* | 2/2013 | Heanue ............ G01J 3/02 600/322 |
| 2013/0203082 A1 | 8/2013 | Gonda et al. |
| 2013/0203083 A1* | 8/2013 | Connors ........... G01N 33/6893 435/7.92 |
| 2013/0230866 A1 | 9/2013 | Miyashita et al. |
| 2013/0245456 A1 | 9/2013 | Ferguson, Jr. et al. |
| 2013/0286176 A1 | 10/2013 | Westwick et al. |
| 2013/0296715 A1 | 11/2013 | Lasser et al. |
| 2013/0342674 A1 | 12/2013 | Dixon |
| 2013/0345560 A1 | 12/2013 | Ferguson, Jr. et al. |
| 2014/0099007 A1 | 4/2014 | Sarkar et al. |
| 2014/0254909 A1* | 9/2014 | Carmi .............. A61B 6/032 382/131 |
| 2014/0308656 A1 | 10/2014 | Flower |
| 2014/0316262 A1 | 10/2014 | Havens |
| 2014/0371583 A1* | 12/2014 | Flower ............. A61B 5/0275 600/431 |
| 2015/0112192 A1* | 4/2015 | Docherty .......... A61B 1/042 600/431 |
| 2015/0112193 A1 | 4/2015 | Docherty et al. |
| 2015/0164396 A1* | 6/2015 | Acharya ........... A61B 5/1455 600/322 |
| 2015/0182137 A1* | 7/2015 | Flower ............. A61B 5/0275 600/431 |
| 2015/0196208 A1 | 7/2015 | Dvorsky et al. |
| 2015/0230710 A1 | 8/2015 | Nahm et al. |
| 2015/0230715 A1 | 8/2015 | Nahm et al. |
| 2015/0248758 A1* | 9/2015 | Pautot ............. G06T 7/20 382/131 |
| 2015/0381909 A1 | 12/2015 | Butte et al. |
| 2016/0038027 A1 | 2/2016 | Brzozowski et al. |
| 2016/0041098 A1 | 2/2016 | Hirawake et al. |
| 2016/0097716 A1* | 4/2016 | Gulati ............. A61B 5/02416 250/339.01 |
| 2016/0199515 A1 | 7/2016 | Flower |
| 2016/0253800 A1* | 9/2016 | Gurevich .......... A61B 5/0071 382/128 |
| 2016/0371834 A1 | 12/2016 | Watanabe et al. |
| 2017/0039710 A1 | 2/2017 | Minai et al. |
| 2017/0084024 A1* | 3/2017 | Gurevich .......... A61B 5/0071 |
| 2017/0245766 A1* | 8/2017 | Flower ............. A61B 5/02416 |
| 2017/0303800 A1* | 10/2017 | Flower ............. A61B 5/0261 |
| 2018/0020933 A1 | 1/2018 | Dvorsky et al. |
| 2018/0104362 A1 | 4/2018 | Golijanin et al. |
| 2018/0120230 A1 | 5/2018 | Moriyama et al. |
| 2018/0220907 A1 | 8/2018 | Dvorsky et al. |
| 2018/0234603 A1 | 8/2018 | Moore et al. |
| 2018/0369426 A1 | 12/2018 | Flower et al. |

FOREIGN PATENT DOCUMENTS

| | | |
|---|---|---|
| CA | 2413033 A1 | 3/2000 |
| CA | 2711560 A1 | 7/2009 |
| CA | 2913692 A1 | 1/2015 |
| CN | 1049781 A | 3/1991 |
| CN | 1200174 A | 11/1998 |
| CN | 1399528 A | 2/2003 |
| CN | 101264014 A | 9/2008 |
| CN | 101451953 A | 6/2009 |
| CN | 102288589 A | 12/2011 |
| CN | 102405212 A | 4/2012 |
| CN | 102436648 A | 5/2012 |
| CN | 103608662 A | 2/2014 |
| DE | 3906860 A1 | 9/1989 |
| DE | 19608027 A1 | 9/1996 |
| DE | 10028233 A1 | 1/2002 |
| DE | 10120980 A1 | 11/2002 |
| DE | 69727220 T2 | 12/2004 |
| DE | 102005044531 A1 | 3/2007 |
| EP | 0091805 A2 | 10/1983 |
| EP | 0215772 A2 | 3/1987 |
| EP | 0512965 A1 | 11/1992 |
| EP | 0792618 A1 | 9/1997 |
| EP | 0807402 A1 | 11/1997 |
| EP | 0826335 A1 | 3/1998 |
| EP | 1677097 A1 | 7/2006 |
| EP | 1761171 | 3/2007 |
| EP | 1874181 | 1/2008 |
| FR | 2944104 A1 | 10/2010 |
| GB | 2203831 A | 10/1988 |
| JP | S52-34584 A | 3/1977 |
| JP | S58-222331 A | 12/1983 |
| JP | S59-069721 A | 4/1984 |
| JP | S59-070903 A | 4/1984 |
| JP | H01-236879 A | 9/1989 |
| JP | 02-200237 A | 8/1990 |
| JP | H03-115958 A | 5/1991 |
| JP | 04-297236 A | 10/1992 |
| JP | H05-64232 A | 10/1993 |
| JP | H06-007353 A | 1/1994 |
| JP | 06-335451 A | 12/1994 |
| JP | H07-043303 A | 2/1995 |
| JP | 07-065154 A | 3/1995 |
| JP | 07-079955 A | 3/1995 |
| JP | H07-155285 A | 6/1995 |
| JP | H07-155286 A | 6/1995 |
| JP | H07-155290 A | 6/1995 |
| JP | H07-155291 A | 6/1995 |
| JP | H07-155292 A | 6/1995 |
| JP | 07-222712 A | 8/1995 |
| JP | H07-204156 A | 8/1995 |
| JP | H07-222723 A | 8/1995 |
| JP | H07-250804 A | 10/1995 |
| JP | H07-250812 A | 10/1995 |
| JP | 08-024227 A | 1/1996 |
| JP | H08-224208 A | 9/1996 |
| JP | H08-224209 A | 9/1996 |
| JP | H08-224240 A | 9/1996 |
| JP | H09-120033 A | 5/1997 |
| JP | H09-305845 A | 11/1997 |
| JP | H09-308609 A | 12/1997 |
| JP | H09-309845 A | 12/1997 |
| JP | H10-500479 A | 1/1998 |
| JP | H10-503480 A | 3/1998 |
| JP | H10-085222 A | 4/1998 |
| JP | H10-104070 A | 4/1998 |
| JP | H10-151104 A | 6/1998 |

(56) References Cited

FOREIGN PATENT DOCUMENTS

| | | |
|---|---|---|
| JP | H10-506440 A | 6/1998 |
| JP | H10-506550 A | 6/1998 |
| JP | H10-201700 A | 8/1998 |
| JP | H10-201707 A | 8/1998 |
| JP | H11-137517 A | 5/1999 |
| JP | H11-155812 A | 6/1999 |
| JP | H11-509748 A | 8/1999 |
| JP | 2001-198079 A | 7/2001 |
| JP | 2002-219129 A | 8/2002 |
| JP | 2003-510121 A | 3/2003 |
| JP | 2003-144401 A | 5/2003 |
| JP | 2003-187226 A | 7/2003 |
| JP | 2003-329589 A | 11/2003 |
| JP | 2004-528917 A | 9/2004 |
| JP | 2004-325200 A | 11/2004 |
| JP | 2006-503620 A | 2/2006 |
| JP | 2006-192280 A | 7/2006 |
| JP | 2007-021006 A | 2/2007 |
| JP | 3896176 B2 | 3/2007 |
| JP | 2008-023113 A | 2/2008 |
| JP | 2008-525126 A | 7/2008 |
| JP | 2008-220926 A | 9/2008 |
| JP | 2008-535600 A | 9/2008 |
| JP | 2008-231113 A | 10/2008 |
| JP | 2009-095683 A | 5/2009 |
| JP | 2009-519082 A | 5/2009 |
| JP | 2009-291554 A | 12/2009 |
| JP | 2010-505582 A | 2/2010 |
| JP | 2010-521267 A | 6/2010 |
| JP | 2011-509768 A | 3/2011 |
| JP | 2011-519589 A | 7/2011 |
| JP | 2011-528918 A | 12/2011 |
| JP | 5918532 B2 | 5/2016 |
| JP | 2016-521612 A | 7/2016 |
| KR | 90-0005434 B1 | 7/1990 |
| KR | 2002-0064287 A | 8/2002 |
| RU | 2288633 C1 | 12/2006 |
| WO | WO-1986/02730 A1 | 5/1986 |
| WO | WO-1990/10219 A1 | 9/1990 |
| WO | WO-1990/12536 A1 | 11/1990 |
| WO | WO-1993/25141 A1 | 12/1993 |
| WO | WO-1994/12092 A1 | 6/1994 |
| WO | WO-1995/00171 A1 | 1/1995 |
| WO | WO-1995/26673 A2 | 10/1995 |
| WO | WO-1996/09435 A1 | 3/1996 |
| WO | WO-1996/09792 A1 | 4/1996 |
| WO | WO-1996/18415 A1 | 6/1996 |
| WO | WO-1996/23524 A1 | 8/1996 |
| WO | WO-1996/39925 A1 | 12/1996 |
| WO | WO-1997/08538 A1 | 3/1997 |
| WO | WO-1998/24360 A1 | 6/1998 |
| WO | WO-1998/30144 A1 | 7/1998 |
| WO | WO-1998/46122 A1 | 10/1998 |
| WO | WO-1999/00053 A1 | 1/1999 |
| WO | WO-1999/47940 A1 | 9/1999 |
| WO | WO-1999/53832 A1 | 10/1999 |
| WO | WO-2000/42910 A1 | 7/2000 |
| WO | WO-2000/47107 A1 | 8/2000 |
| WO | WO-2001/08552 A1 | 2/2001 |
| WO | WO-2001/17561 A1 | 3/2001 |
| WO | WO-2001/22870 A1 | 4/2001 |
| WO | WO-2001/39764 A2 | 6/2001 |
| WO | WO-2001/69244 A2 | 9/2001 |
| WO | WO-2001/80734 A1 | 11/2001 |
| WO | WO-2001/82786 A2 | 11/2001 |
| WO | WO-2002/061390 A2 | 8/2002 |
| WO | WO-2003/006658 A1 | 1/2003 |
| WO | WO-2004/006963 A1 | 1/2004 |
| WO | WO-2004/052195 A1 | 6/2004 |
| WO | WO-2005/026319 A2 | 3/2005 |
| WO | WO-2005/034747 A1 | 4/2005 |
| WO | WO-2005/036143 A1 | 4/2005 |
| WO | WO-2005/079238 A2 | 9/2005 |
| WO | WO-2006/111836 A1 | 10/2006 |
| WO | WO-2006/111909 A1 | 10/2006 |
| WO | WO-2006/116634 A2 | 11/2006 |
| WO | WO-2006/119349 A2 | 11/2006 |
| WO | WO-2006/121631 A2 | 11/2006 |
| WO | WO-2006/121631 A3 | 11/2006 |
| WO | WO-2006/123742 A1 | 11/2006 |
| WO | WO-2007/028032 A2 | 3/2007 |
| WO | WO-2008/039968 A2 | 4/2008 |
| WO | WO-2008/044822 A1 | 4/2008 |
| WO | WO-2008/070269 A2 | 6/2008 |
| WO | WO-2008/070269 A3 | 6/2008 |
| WO | WO-2008/087869 A1 | 7/2008 |
| WO | WO-2009/046985 A2 | 4/2009 |
| WO | WO-2009/046985 A3 | 4/2009 |
| WO | WO-2009/048660 A2 | 4/2009 |
| WO | WO-2009/092162 A1 | 7/2009 |
| WO | WO-2009/127972 A2 | 10/2009 |
| WO | WO-2012/038824 A1 | 3/2012 |
| WO | WO-2012/096878 A2 | 7/2012 |
| WO | WO-2013/190391 A2 | 12/2013 |
| WO | WO-2015/001427 A2 | 1/2015 |
| WO | WO-2013/002350 A1 | 2/2015 |

OTHER PUBLICATIONS

Alander, J.T. et al. (Jan. 1, 2012). "A Review of Indocyanine Green Fluorescent Imaging in Surgery," *International Journal of Biomedical Imaging* 2012:1-26, article ID 940585. Jarmo T. Alander et al.; A Review of Indocyanine Green Fluorescent Imaging in Surgery; International Journal of Biomedical Imaging, vol. 2, No. 7, Jan. 1, 2012, pp. 2068-2026.

Alfano et al. (Oct. 1987). "Fluorescence Spectra from Cancerous and Normal Human Breast and Lung Tissues," *IEEE Journal of Quantum Electronics* QE-23(10):1806-1811.

Alm, A. et al. (Jan. 1, 1973). "Ocular and Optic Nerve Blood Flow at Normal and Increased Intraocular Pressures in Monkeys (*Macaca irus*): A Study with Radioactively Labelled Microspheres Including Flow Determinations in Brain and Some Other Tissues," *Experimental Eye Research* 15(1):15-29.

Alonso-Burgos, A. et al.(2006). "Preoperative planning of deep inferior epigastric artery perforator flap reconstruction with multislice-CT angiography: imaging findings and initial experience," *Journal of Plastic, Reconstructive & Aesthetic Surgery* 59:585-593.

Alvarez, F. J. et al. (Apr. 1996). "Behaviour of Isolated Rat and Human Red Blood Cells Upon Hypotonic-Dialysis Encapsulation of Carbonic Anhydrase and Dextran," *Biotechnology and Applied Biochemistry* 23(2):173-179.

Ancalmo, N. et al. (1997). "Minimally invasive coronary artery bypass surgery: really minimal?" *Ann. Thorac. Surg.* 64:928-929.

Andersson-Engels, S. et al. (1991). "Fluorescence Characteristics of Atherosclerotic Plaque and Malignant Tumors," in *Optical Methods for Tumor Treatment and Early Diagnosis: Mechanisms and Techniques*, T. J. Dougherty (Ed.), The Society of Photo-optical Instrumentation Engineers (SPIE) 1426:31-43, fourteen pages.

Andersson-Engels, S. et al. (Mar. 1989). "Tissue Diagnostics Using Laser-Induced Fluorescence," *Berichte der Bunsengesellschaft für physikalische Chemie* 93(3):335-342.

Angelov, D.N. et al. (Apr. 1999). "Contralateral Trigeminal Nerve Lesion Reduces Polyneuronal Muscle Innervation after Facial Nerve Repair in Rats," *European Journal of Neuroscience* 11(4):1369-1378.

Annese, V. et al. (2005). "Erthrocytes-Mediated Delivery of Dexamethasone in Steroid-Dependent IBD Patients—a Pilot Uncontrolled Study," *American Journal of Gastroenterology* 100:1370-1375.

Argus-50/CA, Inter cellular CA2+ (calcium ion) Image Analysis system (Feb. 1992). "Observation and 2-dimensional analysis of Ca2+ concentration distribution. Fura-2 and Indo-1 compatible. Ca2+ concentrations are calculated from the fluorescence ratio," pp. 1-10.

Australian Notice of Allowance dated Sep. 17, 2018 for Australian Patent Application No. 2015327665, filed on Mar. 23, 2017, three pages.

(56) References Cited

OTHER PUBLICATIONS

Australian Notice of Allowance dated Jul. 3, 2019 for Australian Patent Application No. 2014408488, filed on Mar. 31, 2017, three pages.
Australian Office Action dated Jun. 26, 2018 for Australian Patent Application No. 2014408488, filed on Mar. 31, 2017, nine pages.
Author Unknown. (Jun. 4, 2008)."Invitrogen," Material Safety Data Sheet, p. 1-4.
Awano, T. et al. (Jun. 2010). "Intraoperative EC-IC Bypass Blood Flow Assessment with Indocyanine Green Angiography in Moyamoya and Non-moyamoya Ischemic Stroke," *World Neurosurg.* 73(6):668-674.
Azuma, R. et al. (2008, presented in part Jun. 2007). "Detection of Skin Perforators by Indocyanine Green Fluorescence Nearly Infrared Angiography," *PRS Journal* 122(4):1062-1067.
Balacumarswami, L. et al. (Aug. 2004). "Does Off-Pump Total Arterial Grafting Increase the Incidence of Intraoperative Graft Failure?," *The Journal of Thoracic and Cardiovascular Surgery* 128(2):238-244.
Barton, J.K. et al. (1999) "Simultaneous irradiation and imaging of blood vessels during pulsed laser delivery," *Lasers in Surgery and Medicine* 24(3):236-243.
Bassingthwaighte, J.B. et al. (Apr. 1974). "Organ Blood Flow, Wash-in, Washout, and Clearance of Nutrients and Metabolites," *Mayo Clin. Proc.* 49(4):248-255.
Batliwala, H. et al. (Apr. 15, 1995). "Methane-Induced Haemolysis of Human Erythrocytes," *Biochemical J.* 307(2):433-438.
Baumgartner, R. et al. (1987). "Section V—In vivo Localization and Photodynamic Therapy: A Fluorescence Imaging Device for Endoscopic Detection of Early Stage Cancer—Instrumental and Experimental Studies," *Photochemistry and Photobiology* 46(5):759-763.
Baumgartner, R. et al. (Jan. 1, 1990). "A Fluorescence Imaging Device for Endoscopic Detection of Early Stage Cancer Instrumental and Experimental Studies," Section Five in *SPIE* Press, ed. Abraham Katzir, pp. 513-517, eight pages.
Bek, T. (1999). "Diabetic Maculopathy Caused by Disturbances in Retinal Vasomotion: A New Hypothesis," *Acta Ophthalmologica Scandinavica* 77:376-380.
Benson, R.C. et al. (1978). "Fluorescence Properties of Indocyanine Green as Related to Angiography," *Phys. Med. Biol.* 23(1):159-163.
Black's Medical Dictionary, "Perfusion," 42nd Edition (2009), two pages.
Boer, F.et al. (1994). "Effect of Ventilation on First-Pass Pulmonary Retention of Alfentaril and Sufentanil in Patients Undergoing Coronary Artery Surgery," *British Journal Anesthesia* 73:458-463.
Boldt, .J. et al. (Feb. 1990). "Lung management during cardiopulmonary bypass: influence on extravascular lung water," *Journal of Cardiothoracic Anesthesia* 4(1):73-79.
Boldt, J. et al. (1991). "Does the technique of cardiopulmonary bypass affect lung water content?" *European Journal of Cardio-Thoracic Surgery* 5:22-26.
Brazilian Office Action dated May 14, 2019 for Brazilian Application No. PI 0907272-1, filed on Oct. 14, 2010, five pages.
Bütter, A. et al. (May 2005). "Melanoma in Children and the Use of Sentinel Lymph Node Biopsy," *Journal of Pediatric Surgery* 40(5):797-800.
C2741, Compact High Performance video camera for industrial applications with Built-in contrast enhancement circuit, Jun. 1998, six pages.
Canada Health. (1997). "Coronary Bypass Surgery and Angioplasty, 1982-1995, Heart Disease and Stroke in Canada," Canada Health, located at <http:/www.hc-sc.gc.ca/hpb>, eighty two pages.
Canadian Notice of Allowance dated Jan. 4, 2018 for Canadian Application No. 2,750,760, filed on Jul. 25, 2008, one page.
Canadian Notice of Allowance dated Sep. 27, 2017 for Canadian Application No. 2,811,847, filed on Mar. 20, 2013, one page.
Canadian Office Action dated Dec. 12, 2018 for CA Application No. 2,963,987 filed on Mar. 27, 2017, four pages.
Canadian Office Action dated Dec. 28, 2018 for CA Application No. 2,963,450 filed on Apr. 3, 2017, four pages.
Canadian Office Action dated Feb. 13, 2018 for CA Application No. 2,963,450 filed on Apr. 3, 2017, three pages.
Canadian Office Action dated Feb. 27, 2017 for Canadian Application No. 2,750,760, filed on Jul. 25, 2011, three pages.
Canadian Office Action dated Feb. 28, 2018 for CA Application No. 2,963,987 filed on Mar. 27, 2017, five pages.
Canadian Office Action dated Jan. 19, 2017 for Canadian Application No. 2,914,778 filed on Dec. 8, 2015, four pages.
Canadian Office Action dated Mar. 16, 2016 for CA Application No. 2,750,760 filed on Jan. 23, 2009, five pages.
Canadian Office Action dated May 28, 2019 for Canadian Application No. 3,011,310, filed on Jul. 11, 2018, four pages.
Canadian Office Action dated Nov. 28, 2017 for Canadian Application No. 2,914,778 filed on Dec. 8, 2015, six pages.
Canadian Office Action dated Nov. 28, 2018 for CA Application No. 2,750,760 filed on Jan. 23, 2009, three pages.
Canadian Office Action dated Oct. 25, 2016 for Canadian Patent Application No. 2,811,847, filed on Sep. 20, 2011, three pages.
Canadian Office Action dated Sep. 30, 2015 for CA Application No. 2,811,847, filed on Sep. 20, 2011, four pages.
Chinese Office Action dated Jul. 3, 2012, issued in counterpart Chinese Application No. 200980123414.0, eight pages.
Chinese Office Action dated Apr. 6, 2017 for Chinese Application No. 201510214021.8, filed on May 14, 2009, fifteen pages.
Chinese Office Action dated Apr. 17, 2019 for Chinese Application No. 201510214021.8, filed on May 14, 2009, sixteen pages.
Chinese Office Action dated Apr. 26, 2019 for CN Application No. 201580064648.8 filed on May 26, 2017, twenty six pages.
Chinese Office Action dated Aug. 8, 2016 for Chinese Application No. 201180057244.8 filed on Sep. 20, 2011, eighteen pages.
Chinese Office Action dated Dec. 19, 2017 for Chinese Application No. 201180057244.8 filed on Sep. 20, 2011, eleven pages.
Chinese Office Action dated Feb. 8, 2018 for Chinese Application No. 201510214021.8, filed on May 14, 2009, seventeen pages.
Chinese Office Action dated Mar. 13, 2017 for Chinese Application No. 201180057244.8 filed on Sep. 20, 2011, twenty pages.
Chinese Office Action dated May 23, 2013, issued in counterpart Chinese Application No. 200980123414.0, nineteen pages.
Chinese Office Action dated Nov. 12, 2015 for Chinese Patent Application No. 201180057244.8, filed on Sep. 20, 2010, five pages, (English Translation).
Chinese Office Action dated Sep. 27, 2018 for Chinese Application No. 201510214021.8, filed on May 14, 2009, seventeen pages.
Coffey, J.H. et al. (1984). "Evaluation of Visual Acuity During Laser Photoradiation Therapy of Cancer," *Lasers in Surgery and Medicine* 4(1):65-71.
Conley, M.P. et al. (Oct. 2004). "Anterograde Transport of Peptide-Conjugated Fluorescent Beads in the Squid Giant Axom Identifies a Zip-Code for Synapse," *Biological Bulletin* 207(2):164, one page.
Costa, R.A. et al. (Oct. 2001). "Photodynamic Therapy with Indocyanine Green for Occult Subfoveal Choroidal Neovascularization Caused by Age-Related Macular Degeneration," *Curr. Eye Res.* 23(4):274-275.
Cothren, R.M. et al. (Mar. 1990). "Gastrointestinal Tissue Diagnosis by Laser-Induced Fluorescence Spectroscopy at Endoscopy," *Gastrointestinal Endoscopy* 36(2):105-111.
Dail, W.G. et al. (Oct. 1999). "Multiple Vasodilator Pathways from the Pelvic Plexus to the Penis of the Rat," *International Journal of Impotence Research* 11(5):277-285.
Dan, A.G. et al. (Nov. 2004). "1% Lymphazurin vs 10% Fluorescein for Sentinel Node Mapping in Colorectal Tumors," *Arch Surg.* 139(11):1180-1184.
Daniels, G. et al. (Apr. 2007). "Towards Universal Red Blood Cell," *Nature Biotechnology* 25(4):427-428.
De Flora, A. (Sep. 1986). "Encapsulation of Adriamycin in human erythrocytes," *Proc. Natl. Acad. Sci.*, USA 83(18):7029-7033.
Declaration of Brian Wilson dated Aug. 22, 2017 for Inter Partes Review No. IPR2017-01426, twelve pages.
Definition of "Expose," Excerpt of Merriam Webster's Medical Desk Dictionary (1993), four pages.
Definition of "Graft," Excerpt of Stedman's Medical Dictionary for the Health Professions and Nursing; 6th Ed. (2008), three pages.

(56) References Cited

OTHER PUBLICATIONS

De-Grand, A.M. et al. (Dec. 2003). "An Operational Near Infrared Fluorescence Imaging System Prototype for Large Animal Surgery," *Technology in Cancer Research & Treatment* 2(6):1-10.

Deloach, J.R. (ed.) et al. (1985). *Red Blood Cells as Carriers for Drugs. A Method for Disseminating Chemotherapeutics, Hormones, Enzymes and Other Therapeutic Agents via the Circulatory System*, Karger, Basel, CH, pp. v-vii, (Table of Contents), seven pages.

Deloach, J.R. (Jun. 1983). "Encapsulation of Exogenous Agents in Erythrocytes and the Circulating Survival of Carrier Erythrocytes," *Journal of Applied Biochemistry* 5(3):149-157.

Demos (May/Jun. 2004). "Near-Infrared Autofluorescence Imaging for Detection of Cancer," *Journal of Biomedical Optics* 9(3):587-592.

Desai, N.D. et al. (Oct. 18, 2005, e-published on Sep. 28, 2005) "Improving the Quality of Coronary Bypass Surgery with Intraoperative Angiography," *Journal of the American College of Cardiology* 46(8):1521-1525.

Detter, C. et al. (Aug. 28, 2007). "Fluorescent Cardiac Imaging: A Novel Intraoperative Method for Quantitative Assessment of Myocardial Perfusion During Graded Coronary Artery Stenosis," *Circulation* 116(9):1007-1014.

Detter, C. et al. (Jun. 2002). "Near-Infrared Fluorescence Coronary Angiography: A New Noninvasive Technology for Intraoperative Graft Patency Control." *The Heart Surgery Forum* #2001-6973 5(4):364-369.

Dietz, F.B. et al. (Feb. 2003). "Indocyanine Green: Evidence of Neurotoxicity in Spinal Root Axons," *Anesthesiology* 98(2):516-520.

Digital CCD Microscopy (date unknown). Chapter 14, pp. 259-282.

Dougherty, T.J. et al. (1990). "Cutaneous Phototoxic Occurrences in Patients Receiving Photofrin," *Lasers in Surgery and Medicine* 10(5):485-488.

Draijer, M.J. et al. (Jun. 17-19, 2007). "Laser Doppler Perfusion Imaging with a High-Speed CMOS-Camera," in *Novel Optical Instrumentation for Biomedical Applications III*, C. Depeursinge, ed., Proceedings of SPIE-OSA Biomedical Optics (Optical Society of America, 2007), SPIE-OSA, 6631:0N1-0N7, eight pages.

Dünne, A. et al. (Nov. 2001)."Value of Sentinel lymphonodectomy in Head and Neck Cancer Patients without Evidence of Lymphogenic Metastatic Disease," *Auris Nasus Larynx* 28(4):339-344.

Ekstrand, M.I. et al. (Feb. 14, 2008). "The Alpha-Herpesviruses: Molecular Pathfinders in Nervous System Circuits," *Trends in Molecular Medicine, Elsevier Current Trends* 14(3):134-140.

Emery R.W. et al. (Aug. 1996). "Revascularization Using Angioplasty and Minimally Invasive Techniques Documented by Thermal Imaging," *The Annals of Thoracic Surgery* 62(2):591-593.

Enquist, L.W. et al. (2002). "Directional Spread of an α-Herpesvirus in the Nervous System," *Veterinary Microbiology* 86:5-16.

Eren, S. et al. (Dec. 1995). "Assessment of Microcirculation of an Axial Skin Flap Using Indocyanine Green Fluorescence Angiography," *Plast. Reconstr. Surg.* 96(7):1636-1649.

European Decision in Opposition Proceeding Revoking (Jun. 10, 2010). European Patent No. 1 143 852, thirty pages.

European Decision of European Patent Office Technical Board of Appeal Revoking Counterpart Patent No. 1143852, dated Oct. 23, 2013.

European Notice of Allowance dated Jul. 16, 2019 for EP Application No. 18166591.0, filed on May 1, 2009, eight pages.

European Notice of Allowance dated Apr. 21, 2017 for EP Application No. 09732993.2, filed on Nov. 8, 2010, two pages.

European Notice of Allowance dated Dec. 1, 2017 for European patent Application No. 09739980.2, filed on Nov. 30, 2010, seven pages.

European Notice of Allowance dated Mar. 15, 2018 for EP Application No. 09739980.2 filed on Nov. 30, 2010, two pages.

European Notice of Allowance dated Nov. 21, 2017 for European Patent Application No. 15160177.0, filed on Aug. 11, 2000, seven pages.

European Notice of Allowance dated Oct. 21, 2015 for EP Application No. 11 826 475.3, filed on Sep. 20, 2010, eight pages.

European Notice of Allowance dated Oct. 29, 2015 for EP Application No. 09 704 642.9, filed on Jan. 25, 2008, two pages.

European Office Action dated Apr. 6, 2018 for EP Application No. 15188378.2 filed on Oct. 5, 2015, four pages.

European Office Action dated Aug. 31, 2017 for EP Application No. 09739980.2 filed on Nov. 30, 2010, four pages.

European Office Action dated Mar. 9, 2016 for European Patent Application No. 09739980.2 filed on May 1, 2009, five pages.

European Office Action dated Mar. 27, 2015 for EP Application No. 09 732 993.2, filed on Apr. 14, 2008, six pages.

European Office Action dated May 15, 2014 in EP Application No. 09732993.2 , one page.

European Office Action dated May 27, 2016 for EP Application No. 15160177.0 filed on Aug. 11, 2000, five pages.

European Office Action dated May 28, 2018 for EP Application No. 16183434.6 filed on Aug. 9, 2016, four pages.

European Office Action dated Nov. 14, 2016 in EP Application No. 16163909.1, two pages.

European Office Action dated Sep. 21, 2017 for European Application No. 16163909.1 filed on Apr. 5, 2016, three pages.

European Opposition of European Patent No. EP1143852 lodged by Hamamatsu Photonics, Inc., Jul. 30, 2008.

European Notice of Allowance dated Sep. 26, 2019, for Patent Application No. 16163909.1, filed Jan. 25, 2008.

European Search Report dated Apr. 28, 2014 for EP Application No. 09 732 993.2, filed on Apr. 14, 2008, eight pages.

European Search Report dated Dec. 16, 2010 for European Application No. 10186218.3 filed on Aug. 11, 2000, seven pages.

European Search Report dated Feb. 22, 2012 for EP Application No. 09 704 642.9, filed on Jan. 25, 2008, fifteen pages.

European Search Report dated Jan. 10, 2018 for EP Application No. 17171383.7 filed on May 16, 2017, eleven pages.

European Search Report dated Jan. 28, 2014 for EP Application No. 11 826 475.3, filed on Sep. 20, 2010, six pages.

European Search Report dated Jul. 6, 2004 for EP Application No. 00955472.6 filed on Aug. 11, 2000, five pages.

European Search Report dated Jul. 16, 2018 for EP Application No. 15846111.1, filed on Apr. 25, 2017, thirteen pages.

European Search Report dated Jun. 6, 2018 for EP Application No. 18166591.0 filed on Apr. 10, 2018, six pages.

European Search Report dated Jun. 11, 2014 for European Application No. 13178642.8, filed on May 1, 2009, five pages.

European Search Report dated Jun. 28, 2016 for European Application No. 16163909.1 filed on Apr. 5, 2016, six pages.

European Search Report dated May 23, 2018 for EP Application No. 14903635.2 filed on May 2, 2017, nine pages.

European Search Report dated Oct. 14, 2015 for EP Application No. 13806313.6 filed on Jun. 20, 2013, nine pages.

European Search Report dated Sep. 16, 2016 for EP Application No. 16183434.6 filed on Aug. 9, 2016, ten pages.

European Summons to attend Oral Proceedings pursuant to Rule 115(1) EPC dated Apr. 25, 2016 for European patent application No. 09732993.2, filed on Apr. 14, 2009, 5 pages.

European Summons to attend Oral Proceedings pursuant to Rule 115(1) EPC dated Dec. 16, 2016 for European patent application No. 15160177.0, filed on Aug. 11, 2000, seven pages.

European Summons to Attend the Oral Proceedings dated May 31, 2019 for European Application No. 16163909.1 filed on Apr. 5, 2016, two pages.

European Summons to Attend the Oral Proceedings dated Oct. 24, 2018 for European Application No. 16163909.1 filed on Apr. 5, 2016, four pages.

Falk, T. et al. (Apr. 15, 2001). "A Herpes Simplex Viral Vector Expressing Green Fluorescent Protein can be Used to Visualize Morphological Changes in High-density Neuronal Culture," *Electronic Journal of Biotechnology* 4(1):34-45.

Flower, R. et al. (Apr.-Jun. 1999). "Effects of free and liposome-encapsulated hemoglobin on choroidal vascular plexus blood flow, using the rabbit eye as a model system," *European Journal of Ophthalmology* 9(2):103-114.

(56) References Cited

OTHER PUBLICATIONS

Flower, R.W. (1992)."Choroidal Angiography Today and Tomorrow," *Retina* 12(3):189-190.
Flower, R.W. (Apr. 2000). "Experimental Studies of Indocyanine Green Dye-Enhanced Photocoagulation of Choroidal Neovascularization Feeder Vessels," *American Journal of Ophthalmology* 129(4):501-512.
Flower, R.W. (Aug. 2002). "Optimizing Treatment of Choroidal Neovascularization Feeder Vessels Associated with Age-Related Macular Degeneration," *American Journal of Ophthalmology* 134(2):228-239.
Flower, R.W. (Dec. 1973). "Injection Technique for Indocyanine Green and Sodium Fluorescein Dye Angiography of the Eye," *Investigative Opthamology* 12(12):881-895.
Flower, R.W. (Sep. 1, 1994). "Does Preinjection Binding of Indocyanine Green to Serum Actually Improve Angiograms?," *Arch Ophthalmol.* 112(9):1137-1139.
Flower, R.W. et al. (Aug. 1977). "Quantification of Indicator Dye Concentration in Ocular Blood Vessels," *Exp. Eye Res.* 25(2):103-111.
Flower, R.W. et al. (Dec. 1, 2008, e-published Aug. 15, 2008). "Observation of Erythrocyte Dynamics in the Retinal Capillaries and Choriocapillaris Using ICG-Loaded Erythrocyte Ghost Cells," *Investigative Ophthalmology, & Visual Science* 49(12):5510-5516.
Flower, R.W. et al. (Mar. 26, 2008-Mar. 29, 2008). "Observation of Erythrocyte Dynamics in the Retinal Capillaries and Choriocapillaris Using ICG-Loaded Erythrocyte Ghost Cells," Annual Meeting of the Macula Society, Abstract No. XP002535355, Palm Beach, FL, USA, fourteen pages, (Schedule of the Meeting only).
Forrester et al. (Nov. 1, 2002). "Comparison of Laser Speckle and Laser Doppler Perfusion Imaging: Measurement in Human Skin and Rabbit Articular Tissue," *Medical and Biological Engineering and Computing* 40(6):687-697.
Frangioni, J.V. (Oct. 2003). "In Vivo Near-Infrared Fluorescence Imaging," *Current Opinion in Chemical Biology* 7(5):626-634.
Frenzel H. et al. (Apr. 18, 2008). "In Vivo Perfusion Analysis of Normal and Dysplastic Ears and its Implication on Total Auricular Reconstruction," *Journal of Plastic, Reconstructive and Aesthetic Surgery* 61(Supplement1):S21-S28.
Fritzsch, B. et al. (Aug. 1991)."Sequential Double Labeling With Different Fluorescent Dyes Coupled to Dextran Amines as a Tool to Estimate the Accuracy of Tracer Application and of Regeneration," *Journal of Neuroscience Methods* 39(1):9-17.
Gagnon, A.R. et al. (2006). "Deep and Superficial Inferior Epigastric Artery Perforator Flaps," *Cirugia Plástica Ibero-Latinoamericana* 32(4):7-13.
Gardner, T.J. (1993). "Coronary Artery Disease and Ventricular Aneurysms," in *Surgery, Scientific Principles and Practice*, Greenfield, L.J. (ed.) et al., J.B. Lippincott Co., Philadelphia, PA, pp. 1391-1411, twenty three pages.
Garrett, W.T. et al. (Jul. 8, 1991). "Fluoro-Gold's Toxicity makes it Inferior to True Blue for Long-Term Studies of Dorsal Root Ganglion Neurons and Motoneurons," *Neuroscience Letters* 128(1):137-139.
Geddes, C. D. et al. (2003, e-published on Mar. 20, 2003). "Metal-Enhanced Fluorescence (MEF) Due to Silver Colloids on a Planar Surface: Potential Applications of Indocyanine Green to in Vivo Imaging," *Journal of Physical Chemistry A* 107(18):3443-3449.
Gipponi, M. et al. (Mar. 1, 2004). "New Fields of Application of the Sentinel Lymph Node Biopsy in the Pathologic Staging of Solid Neoplasms: Review of Literature and Surgical Perspectives," *Journal of Surgical Oncology* 85(3):171-179.
Giunta, R.E. et al. (Jul. 2005). "Prediction of Flap Necrosis with Laser Induced Indocyanine Green Fluorescence in a Rat Model," *British Journal of Plastic Surgery* 58(5):695-701.
Giunta, R.E. et al. (Jun. 2000). "The Value of Preoperative Doppler Sonography for Planning Free Perforator Flaps," *Plastic and Reconstructive Surgery* 105(7):2381-2386.

Glossary, Nature, downloaded from the internet <http://www.nature.com/nrg/journal/v4/nl0/glossary/nrgl 183_glossary.html>> HTML on Jun. 30, 2014, three pages.
Glover, J.C. et al. (Nov. 1986). "Fluorescent Dextran-Amines Used as Axonal Tracers in the Nervous System of the Chicken Embryo," *Journal of Neuroscience Methods* 18(3):243-254.
Goldstein, J.A. et al. (Dec. 1998). "Intraoperative Angiography to Assess Graft Patency After Minimally Invasive Coronary Bypass," *Ann. Thorac. Surg.* 66(6):1978-1982. [Exhibit 1007].
Gothoskar A.V. (Mar. 2004). "Resealed Erythrocytes: A Review," *Pharmaceutical Technology* pp. 140, 142, 144, 146, 148, 150, 152 and 154-158, twelve pages.
Granzow, J.W. et al. (Jul. 2007)."Breast Reconstruction with Perforator Flaps" *Plastic and Reconstructive Surgery* 120(1):1-12.
Green, H.A. et al. (Jan. 1992). "Burn Depth Estimation Using Indocyanine Green Fluorescence," *Arch Dermatol* 128(1):43-49.
Haglund, M. et al. (Feb. 1996). "Enhanced Optical Imaging of Human Gliomas and Tumor Margins," *Neurosurgery* 38(2):308-317.
Haglund, M.M. et al. (Nov. 1994). "Enhanced Optical Imaging of Rat Gliomas and Tumor Margins," *Neurosurgery* 35(5):930-941.
Hallock, G.G. (Jul. 2003). "Doppler Sonography and Color Duplex Imaging for Planning a Perforator Flap," *Clinics in Plastic Surgery* 30(3):347-357. (Per J. Liebes cite with a later OA e-mail dated Mar. 24, 2016).
Hamamatsu Brochure. (May 1997). Specifications for Real-time Microscope Image Processing System: ARGUS-20 with C2400-75i, four pages [Exhibit 1006].
Hamamatsu. (Date unknown). Microscope Video Camera, For Fluorescent Observation, Easy Fluorescent Image Analysis C2400-731,-75l Series a CCD Camera, seven pages.
Hayashi, J. et al. (Nov. 1993). "Transadventitial Localization of Atheromatous Plaques by Fluorescence Emission Spectrum Analysis of Mono-L Aspartyl-Chlorin e6," *Cardiovascular Research* 27(11):1943-1947.
Hayata, Y. et al. (Jul. 1982). "Fiberoptic Bronchoscopic Laser Photoradiation for Tumor Localization in Lung Cancer," *Chest* 82(1):10-14.
He, Z. (Feb. 2009). "Fluorogold Induces Persistent Neurological Deficits and Circling Behavior in Mice Over-Expressing Human Mutant Tau," *Current Neurovascular Research* 6(1):54-61.
Herts, B.R. (May 2003). "Imaging for Renal Tumors," *Current Opin . . . Urol.* 13(3):181-186.
Hirano, T. et al. (1989). "Photodynamic Cancer Diagnosis and Treatment System Consisting of Pulse Lasers and an Endoscopic Spectro-Image Analyzer," *Laser in Life Sciences* 3(2):99-116.
Holm, C. et al. (2002). "Monitoring Free Flaps Using Laser-Induced Fluorescence of Indocyanine Green: A Preliminary Experience," *Microsurgery* 22(7):278-287.
Holm, C. et al. (Apr. 2003, e-published on Feb. 25, 2003). "Laser-Induced Fluorescence of Indocyanine Green: Plastic Surgical Applications," *European Journal of Plastic Surgery* 26(1):19-25.
Holm, C. et al. (Dec. 1, 2002). "Intraoperative Evaluation of Skin-Flap Viability Using Laser-Induced Fluorescence of Indocyanine Green," *British Journal of Plastic Surgery* 55(8):635-644.
Humblet, V. et al. (Oct. 2005). "High-Affinity Near-Infrared Fluorescent Small-Molecule Contrast Agents for In Vivo Imaging of Prostate-Specific Membrane Antigen," *Molecular Imaging* 4(4):448-462.
Hung, J. et al. (1991). "Autofluorescence of Normal and Malignant Bronchial Tissue," *Lasers in Surgery and Medicine* 11(2):99-105.
Hyvärinen, L. et al. (1980). "Indocyanine Green Fluorescence Angiography." *Acta ophthalmologica* 58(4):528-538. [Exhibit 1014].
Ikeda, S. (Jul. 1989). "Bronichial Telivision Endoscopy," *Chest* 96(1):41S-42S.
Indian Office Action dated Jan. 16, 2018 for Indian Application No. 2993/DELNP/2011, filed on Apr. 25, 2011, eleven pages.
Indian Office Action dated Jul. 28, 2017 for Indian Application No. 1983/MUMNP/2007, filed on Nov. 27, 2007, seven pages.
Indian Office Action dated Sep. 22, 2016 for Indian Application No. 7566/DELNP/2010, filed on Oct. 27, 2010, nine pages.
International Preliminary Report on Patentability dated Aug. 22, 2019, for PCT/CA2017/050564, filed on May 10, 2017, nine pages.

(56) References Cited

OTHER PUBLICATIONS

International Preliminary Examination Report completed on Jul. 1, 2001 for PCT/US00/22088, filed on Aug. 11, 2000, three pages.
International Preliminary Report on Patentability dated Apr. 4, 2017 for PCT Application No. PCT/CA2015/050973 filed on Sep. 28, 2015, six pages.
International Search Report and the Written Opinion of the International Searching Authority, or the Declaration dated Apr. 3, 2008 for PCT/US07/77892, filed on Sep. 7, 2007, ten pages.
International Search Report and Written Opinion dated Jul. 29, 2009 for PCT/US2009/043975 filed on May 14, 2009, eleven pages.
International Search Report and Written Opinion dated Oct. 24, 2017 for PCT Application No. PCT/CA2017/050564 filed on May 10, 2017, fourteen pages.
International Search Report dated Dec. 3, 2009 for PCT Patent Application No. PCT/IB2009/005700, filed on Apr. 14, 2009, three pages.
International Search Report dated Dec. 3, 2015 for PCT Application No. PCT/CA2015/050973 filed on Sep. 28, 2015, three pages.
International Search Report dated Feb. 1, 2012 for PCT Patent Application No. PCT/IB2011/002381, filed on Sep. 20, 2011, five pages.
International Search Report dated Jan. 22, 2014 for PCT Application No. PCT/IB2013/001934, filed on Jun. 20, 2013, four pages.
International Search Report dated Jul. 4, 2008 for PCT Patent Application No. PCT/US2007/080847, filed on Oct. 9, 2007, three pages.
International Search Report dated Jun. 2, 2009 for PCT Application No. PCT/EP2008/008547, filed on Oct. 9, 2008, five pages.
International Search Report dated Jun. 8, 2009 for PCT Patent Application No. PCT/CA2009/000073, filed on Jan. 23, 2009, three pages.
International Search Report dated Oct. 18, 2000 for PCT Application No. PCT/US2000/22088, filed on Aug. 11, 2000, one page.
International Search Report dated Sep. 11, 2009 for Application No. PCT/US2009/042606 filed on May 1, 2009, five pages.
Invitation to Pay Additional Fees and, Where Applicable, Protest Fee dated Jul. 4, 2017 for PCT/CA2017/050564, filed on May 10, 2017, two pages.
Jaber, S.F. et al. (Sep. 1998). "Role of Graft Flow Measurement Technique in Anastomotic Quality Assessment in Minimally Invasive CABG," *Ann. Thorac. Surg.* 66(3):1087-1092.
Jagoe, J.R. et al. (1989). "Quantification of retinal damage during cardiopulmonary bypass," Third International Conference on Image Processing and its Applications (Conf. Publ. No. 307), IEE, pp. 319-323.
Jamis-Dow, C.A. et al. (Mar. 1996). "Small (< or=3-cm) Renal Masses: Detection with CT versus US and Pathologic Correlation," *Radiology* 198(3):785-788.
Japanese Final Office Action dated Feb. 5, 2018 for Japanese Patent Application No. 2016-014503, filed on Jan. 28, 2016, six pages.
Japanese Final Office Action dated Jan. 28, 2019 for Japanese Patent Application No. 2016-014503, filed on Jan. 28, 2016, 3 pages.
Japanese Final Office Action dated Sep. 25, 2018 for Japanese Application No. 2017-518785 filed on Apr. 7, 2017, six pages.
Japanese Notice of Allowance dated Jan. 25, 2019 for Japanese Application No. 2017-518785 filed on Apr. 7, 2017, six pages.
Japanese Notice of Allowance dated Jun. 7, 2019 for Japanese Patent Application No. 2017-516925 filed on Mar. 28, 2017, six pages.
Japanese Notice of Allowance dated Jun. 8, 2018 for Japanese Patent Application No. 2016-203798 filed on Oct. 17, 2016, six pages.
Japanese Notice of Allowance dated Jun. 21, 2019 for Japanese Patent Application No. 2018-129970, filed on Jul. 9, 2018, six pages.
Japanese Notice of Allowance dated May 10, 2019 for Japanese Patent Application No. 2017-205499, filed on Nov. 24, 2017, six pages.
Japanese Notice of Allowance dated Sep. 16, 2016 for Japanese Patent Application No. 2015-517876 filed on Jun. 20, 2013, six pages.
Japanese Notice of Allowance dated Sep. 25, 2017 for Japanese Patent Application No. 2013-529729, filed on Mar. 21, 2013, six pages.
Japanese Office Action dated Sep. 13, 2019 for Japanese Patent Application No. 2018-153572, filed on Oct. 9, 2014, 3 pages.
Japanese Office Action dated Apr. 1, 2016 for Japanese Patent Application No. 2013-529729, filed on Mar. 21, 2013, seven pages.
Japanese Office Action dated Aug. 20, 2018 for Japanese Patent Application No. 2017-205499, filed on Nov. 24, 2017, six pages.
Japanese Office Action dated Feb. 1, 2016 for Japanese Patent Application No. 2015-517876 filed on Jun. 20, 2013, eight pages.
Japanese Office Action dated Jul. 28, 2017 for Japanese Patent Application No. 2016- 203798 filed on Oct. 17, 2016, four pages.
Japanese Office Action dated Jul. 30, 2013, issued in counterpart Japanese Application No. 2011-504574, filed on Apr. 14, 2009, six pages.
Japanese Office Action dated Mar. 3, 2017 for Japanese Patent Application No. 2016-014503, filed on Jan. 28, 2016, ten pages.
Japanese Office Action dated Mar. 19, 2018 for Japanese Application No. 2017-518785 filed Apr. 7, 2017, eight pages.
Japanese Office Action dated Mar. 31, 2017 for Japanese Patent Application No. 2013-529729, filed on Mar. 21, 2013, eleven pages.
Japanese Office Action dated May 7, 2018 for Japanese Patent Application No. 2017-516925 filed on Mar. 28, 2017, four pages.
Japanese Office Action dated Nov. 19, 2018 for Japanese Patent Application No. 2017-516925 filed on Mar. 28, 2017, four pages.
Japanese Office Action dated Sep. 14, 2015 for Japanese Patent Application No. 2011-504574, filed on Apr. 14, 2009, three pages.
Jolion, J. et al. (Aug. 1991). "Robust Clustering with Applications in Computer Vision," *IEEE Transactions on Pattern Analysis and Machine Intelligence* 13(8):791-802.
Kamolz, L.-P. et al. (Dec. 2003). "Indocyanine Green Video Angiographies Help to Identify Burns Requiring Operation," *Burns* 29(8):785-791.
Kapadia, C.R. et al. (Jul. 1990). "Laser-Induced Fluorescence Spectroscopy of Human Colonic Mucosa. Detection of Adenomatous Transformation," *Gastroenterology* 99(1):150-157.
Kato, H. et al. (Jun. 1985). "Early Detection of Lung Cancer by Means of Hematoporphyrin Derivative Fluorescence and Laser Photoradiation," *Clinics in Chest Medicine* 6(2):237-253.
Kato, H. et al. (Jun. 1990). "Photodynamic Diagnosis in Respiratory Tract Malignancy Using an Excimer Dye Laser System," *Journal of Photochemistry and Photobiology, B. Biology* 6(1-2):189-196.
Keon, W.J. et al. (Dec. 1979). "Coronary Endarterectomy: An Adjunct to Coronary Artery Bypass Grafting," *Surgery* 86(6):859-867.
Kim, S. et al. (Jan. 2004, e-published Dec. 7, 2003). "Near-Infrared Fluorescent Type II Quantum Dots for Sentinel Lymph Node Mapping," *Nature Biotechnology* 22(1):93-97.
Kiryu, J. et al. (Sep. 1994). "Noninvasive Visualization of the Choriocapillaris and its Dynamic Filling," *Investigative Ophthalmology & Visual Science* 35(10):3724-3731.
Kitai, T. et al. (Jul. 2005). "Fluorescence Navigation with Indocyanine Green for Detecting Sentinel Lymph Nodes in Breast Cancer," *Breast Cancer* 12(3):211-215.
Kleszcyńska, H. et al. (Mar. 2005). "Hemolysis of Erythrocytes and Erythrocyte Membrane Fluidity Changes by New Lysosomotropic Compounds," *Journal of Fluorescence* 15(2):137-141.
Köbbert, C. et al. (Nov. 2000). "Current Concepts in Neuroanatomical Tracing," *Progress in Neurobiology* 62(4):327-351.
Kokaji, K. et al. (Date Unknown). "Intraoperative Quality Assessment by Using Fluorescent Imaging in Off-pump Coronary Artery Bypass Grafting," *The Department of Cardiovascular Surgery, University of Keio*, Tokyo, Japan, one page (Abstract only).
Kömürcü, F. et al. (Feb. 2005). "Management Strategies for Peripheral Iatrogenic Nerve Lesions," *Annals of Plastic Surgery* 54(2):135-139.
Korean Office Action dated Sep. 25, 2019, for Patent Application No. 10-2017-7011565, filed Sep. 28, 2015, 7 pages, including the English translation.

(56) References Cited

OTHER PUBLICATIONS

Korean Notice of Allowance dated Apr. 27, 2017 for Korean Patent Application No. 10-2016-7007994, filed on Mar. 25, 2016, three pages.
Korean Notice of Allowance dated Apr. 29, 2016 for Korean Patent Application No. 10-2010-7024977, filed on Apr. 14, 2009, three pages.
Korean Notice of Allowance dated May 20, 2019 for Korean Patent Application No. 2019-7005800, filed on Feb. 26, 2019, three pages.
Korean Notice of Allowance dated Nov. 30, 2018 for Korean Patent Application No. 10-2017-7012463, filed on May 8, 2017, three pages.
Korean Office Action dated Apr. 17, 2018 for Korean Patent Application No. 10-2017-7012463, filed on May 8, 2017, six pages.
Korean Office Action dated Dec. 4, 2018 for Korean Patent Application No. 2017-7011565, filed on Apr. 4, 2017, nine pages.
Korean Office Action dated Jun. 25, 2014 in Korean Patent Application No. 10-2013-7035027, filed on May 14, 2009, fifteen pages.
Korean Office Action dated Nov. 30, 2015 for Korean Patent Application No. 10-2010-7024977, filed on Apr. 14, 2009, two pages.
Krishnan, K. G. et al. (Apr. 1, 2005). "The Role of Near-Infrared Angiography in the Assessment of Post-Operative Venous Congestion in Random Pattern, Pedicled Island and Free Flaps", *British Journal of Plastic Surgery* 58(3):330-338.
Kuipers, J.A. et al. (1999). "Recirculatory and Compartmental Pharmacokinetic Modeling of Alfentanil Pigs, the Influence of Cardiac Output," *Anesthesiology* 90(4):1146-1157.
Kupriyanov, V.V. et al. (Nov. 2004; , e-publication Sep. 28, 2004). "Mapping Regional Oxygenation and Flow in Pig Hearts In Vivo Using Near-infrared Spectroscopic Imaging," *Journal of Molecular and Cellular Cardiology* 37(5):947-957.
Kurihara, K. et al. (Jun. 1984). "Nerve Staining with Leucomethylene Blue: An Experimental Study," *Plastic and Reconstruction Surgery* 73(6):960-964.
Kyo, S. (Date Unknown). "Use of Ultrasound Cardiology during Coronary Artery Bypass Surgery," *Heart and Blood Vessel Imaging II*, three pages.
Lam, S. et al. (1991). "Mechanism of Detection of Early Lung Cancer by Ratio Fluorometry," *Lasers in Life Sciences* 4(2):67-73.
Lam, S. et al. (Feb. 1990). "Detection of Early Lung Cancer Using Low Dose Photofrin II," *Chest* 97(2):333-337.
Lam, S. et al. (Jul. 1, 1990). "Detection of Lung Cancer by Ratio Fluorometry With and Without Photofrin II," *Proc. SPIE—Optical Fibers in Medicine V* 11201:561-568.
Lam, S. et al. (Nov. 1-4, 1990). "Fluorescence Imaging of Early Lung Cancer," *Annual International Conference of the IEEE Engineering in Medicine and Biology Society* 12(3):1142-1143.
Lam, S.C. et al. (1993). "Fluorescence Detection," Chapter 20 in *Lung Cancer*, Roth, J.A. (ed.), et al., Blackwell Scientific Publications Inc., 238 Main Street, Cambridge, Massachusetts, 02142, pp. 325-338, sixteen pages.
Lanciego, J.L. et al. (Jun. 1998). "Multiple Neuroanatomical Tracing in Primates," *Brain Research Protocols* 2(4):323-332.
Lanciego, J.L. et al. (Oct. 1998). "Multiple Axonal Tracing: Simultaneous Detection of Three Tracers in the Same Section," *Histochemistry and Cell Biology* 110(5):509-515.
Laub, G.W. et al. (Nov./Dec. 1989). "Experimental Use of Fluorescein for Visualization of Coronary Arteries," *Vascular and Endovascular Surgery* 23(6):454-457.
Lee, E.T. et al. (Mar. 1997). "A New Method for Assessment of Changes in Retinal Blood Flow," *Medical Engineering & Physics* 19(2):125-130.
Leissner, J. et al. (Jan. 2004). "Extended Radical Lymphadenectomy in Patients with Urothelial Bladder Cancer: Results of a Prospective Multicenter Study," *The Journal of Urology* 171(1):139-144.
Leithner, C. (Jul. 14, 2003). "Untersuchung der Sauerstoffkonzentrationsveranderungen in der Mikrozirkulation des Hirnkortex von Ratten bei funktioneller Stimulation mittels Phosphorescence Quenching," [dissertation], Jul. 14, 2003; retrieved from the Internet: <http://edoc.hu-berlin.de/d issertationen/leith nerch ristoph-2003-07-14/>, two hundred and eight pages [English Abstract and Machine Translation].

Li, X. et al. (May 12, 2004). "Method for Retinal Vessel Detection and Diameter Measurement," Presented at Medical Imaging 2004:Image Processing, San Diego, CA, *Proceedings of SPIE* 5370:1746-1754.
Liedberg, F. et al. (2003). "Sentinel-Node-Diagnostik Beim Invasiven (Bladder Cancer and the Sentinel Node Concept)," *Aktuel Urol.* 34:115-118 (English Abstract Only).
Liedberg, F. et al. (Jan. 2006). "Intraoperative Sentinel Node Detection Improves Nodal Staging in Invasive Bladder Cancer," *The Journal of Urology* 175(1):84-89.
Lippincott's New Medical Dictionary. "Perfusion," p. 707 (1897), three pages.
Liptay, M.J. (Mar. 2004). "Sentinel Node Mapping in Lung Cancer," *Annals of Surgical Oncology* 11(Supplement 3):271S-274S.
Little, J.R. et al. (May 1979). "Superficial Temporal Artery to Middle Cerebral Artery Anastomosis: Intraoperative Evaluation by Fluorescein Angiography and Xenon—133 Clearance," *Journal of Neurosurgery* 50(5):560-569. [Exhibit 1002].
Liu, Q.P. et al. (Apr. 2007). "Bacterial Glycosidases for the Production of Universal Red Blood Cells" *Nature Biotechnology* 25(7):454-464.
Lund, F. et al. (Nov. 1997). "Video Fluorescein Imaging of the Skin: Description of an Overviewing Technique for Functional Evaluation of Regional Cutaneous Blood Evaluation of Regional Cutaneous Perfusion in Occlusive Arterial Disease of the Limbs," *Clinical Physiology* 17(6):619-633.
Mack, M.J. et al. (Sep. 1998). "Arterial Graft Patency in Coronary Artery Bypass Grafting: What Do We Really Know?," *Ann. Thorac. Surg.* 66(3):1055-1059.
Magnani, M. et al. (1998). "Erythrocyte Engineering for Drug Delivery and Targeting," *Biotechnol. Appl. Biochem.* 28:1-6.
Magnani, M. et al. (Jul. 15, 1992). "Targeting Antiretroviral Nucleoside Analogues in Phosphorylated Form to Macrophasges: In Vitro and In Vivo Studies," *Proc. Natl. Acad. Sci. USA* 89(14):6477-6481.
Malmstrom et al. (Nov. 2002). "Early Metastatic Progression of Bladder Carcinoma: Molecular Profile of Primary Tumor and Sentinel Lymph Node," *The Journal of Urology* 168(5):2240-2244.
Malmström, P.U. et al. (Jul. 2004). "Re: Extended Radical Lymphadenectomy in Patients With Urothelial Bladder Cancer: Results of a Prospective Multicenter Study," *J. of Urol.* 172(1):386, one page.
Marangos, N. et al. (Dec. 2001). "In Vivo Visualization of the Cochlear Nerve and Nuclei with Fluorescent Axonal Tracers," *Hearing Research* 162(1-2):48-52.
Martinez-Pérez, M. et al. (Sep. 19, 1996). "Unsupervised Segmentation Based on Robust Estimation and Cooccurrence Data," *Proceedings of the International Conference on Miage Processing (ICIP) Lausanne* 3:943-945.
Martinez-Perez, M.E. et al. (Aug. 2002). "Retinal Vascular Tree Morphology: A Semi-Automatic Quantification," *IEEE Transactions of Biomedical Engineering* 49(8):912-917.
May, S. (May/Jun. 1995). "Photonic Approaches to Burn Diagnostics," *Biophotonics International* pp. 44-50.
Mckee, T.D. et al. (Mar. 1, 2006). "Degradation of Fibrillar Collagen in a Human Melanoma Xenograft Improves the Efficacy of an Oncolytic Herpes Simplex Virus Vector," *Cancer Research* 66(5):2509-2513.
Merriam Webster Medline Plus Medical Dictionary. "Perfusion," located at http://www.merriam-webster.com/medlineplus/perfusion, last visited on Apr. 15, 2015, one page.
Mexican Office Action dated May 30, 2013, issued in counterpart Mexican Application No. Mx/a/2010/011249. no translation.
Minciacchi, D. et al. (Jul. 1991). "A Procedure for the Simultaneous Visualization of Two Anterograde and Different Retrograde Fluorescent Tracers-Application to the Study of the Afferent-Efferent Organization of Thalamic Anterior Intralaminar Nuclei" *Journal of Neuroscience Methods* 38(2-3):183-191.
Mitaka USA, Inc. (2015). "PDE Breast Free Flap Evaluation," located at <http://mitakausa.com/category/pde_education/flaps/>, last visited on Oct. 7, 2016, four pages.
Mitaka USA, Inc. (2015). "PDE-Neo" located at <http://mitakausa.com/pde-neo/>, last visited on Oct. 7, 2016, two pages.

(56) References Cited

OTHER PUBLICATIONS

Mohr, F.W. et al. (May 1997). "Thermal Coronary Angiography: A Method for Assessing Graft Patency and Coronary Anatomy in Coronary Bypass Surgery," *Ann Thorac. Surgery* 63(5):1506-1507.
Montán, S. et al. (Feb. 1, 1985). "Multicolor Imaging and Contrast Enhancement in Cancer-Tumor Localization Using Laser-Induced Fluorescence in Hematoporphyrin-Derivative-Bearing Tissue," *Optics Letters* 10(2):56-58.
Mothes, H. et al. (Nov. 2004). "Indocyanine-Green Fluorescence Video Angiography Used Clinically to Evaluate Tissue Perfusion in Microsurgery," *The Journal of Trauma Injury, Infection, and Critical Care* 57(5):1018-1024.
Motomura, K. et al. (1999). "Sentinel Node Biopsy Guided by Indocyanine Green Dye in Breast Cancer Patients," *Japan J. Clin. Oncol.* 29(12):604-607.
Mullooly, V.M. et al. (1990). "Dihematoporphyrin Ether-Induced Photosensitivity in Laryngeal Papilloma Patients," *Lasers in Surgery and Medicine* 10(4):349-356.
Murphy (2001). "Digital CCD Microscopy," Chapter 14 in *Fundamentals of Light Microscopy and Electronic Imaging*, John Wiley and Sons, pp. i-xi and 259-281.
Nahlieli, O. et al. (Mar. 2001). "Intravital Staining with Methylene Blue as an Aid to Facial Nerve Identification in Parotid Gland Surgery" *J. Oral Maxillofac. Surgery* 59(3):355-356.
Nakamura, T. et al. (1964). "Use of Novel Dyes, Coomassie Blue and Indocyanine Green in Dye Dilution Method," Tohoka University, Nakamura Internal Department, The Tuberculosis Prevention Society, Tuberculosis Research Laboratory, 17(2):1361-1366, seventeen pages.
Nakayama, A. et al. (Oct. 2002). "Functional Near-Infrared Fluorescence Imaging for Cardiac Surgery and Targeted Gene Therapy," *Molecular Imaging* 1(4):365-377.
Naumann, T. et al. (Nov. 15, 2000). "Retrograde Tracing with Fluoro-Gold: Different Methods of Tracer Detection at the Ultrastructural Level and Neurodegenerative Changes of Back-Filled Neurons in Long-Term Studies," *Journal of Neuroscience Methods* 103(1):11-21.
Newman et al. (Oct. 31, 2008). "Update on the Application of Laser-Assisted Indocyanine Green Fluorescent Dye Angiography in Microsurgical Breast Reconstruction," American Society of Plastic Surgeons, Plastic Surgery 2008, 2 pages.
Nimura, H. et al. (May 2004, e-published on Mar. 22, 2004). "Infrared Ray Electronic Endoscopy Combined with Indocyanine Green Injection for Detection of Sentinel Nodes of Patients with Gastric Cancer," *British Journal of Surgery* 91(5):575-579.
Novadaq Technologies Inc. (Jan. 29, 2007). "Novadaq Imaging System Receives FDA Clearance for use During Plastic Reconstructive Surgery," *PR Newswire* three pages.
Novadaq Technologies Inc. (Jan. 19, 2005). 510(k) Summary—Showing X-Ray Fluoroscopy as Predicate Device, Fluorescent Angiographic System, six pages, [Exhibit 1012].
Novadaq Technologies Inc.'s Preliminary Response filed on Aug. 23, 2017 to Petition for Inter Partes Review of U.S. Pat. No. 8,892,190, sixty one pages.
Oddi, A. et al. (Jun. 1996). "Intraoperative Biliary Tree Imaging with Cholyl-Lysyl-Fluorescein: An Experimental Study in the Rabbit" *Surgical Laparoscopy & Endoscopy* 6(3):198-200.
Ogata, F. et al. (Jun. 2007). "Novel Lymphography Using Indocyanine Green Dye for Near-Infrared Fluorescence Labeling," *Annals of Plastic Surgery* 58(6):652-655.
Ohnishi, S. et al. (Jul.-Sep. 2005). "Organic Alternatives to Quantum Dots for Intraoperative Near-Infrared Fluorescent Lymph Node Mapping" *Molecular Imaging* 4(3):172-181.
Ooyama, M. (Oct. 12-15, 1994). The 8th Congress of International YAG Laser Symposium, The 15th Annual Meeting of Japan Society for Laser Medicine, Sun Royal Hotel, Japan, eight pages.
Ott, P. (1998). "Hepatic Elimination of Indocyanine Green with Special Reference to Distribution Kinetics and the Influence of Plasma Protein Binding," *Pharmacology & Toxicology* 83(Supp. II):5-48.
Oxford Concise Medical Dictionary. "Perfusion," p. 571 (1980), three pages.
Pagni, S. et al. (Jun. 1997). "Anastomotic Complications in Minimally Invasive Coronary Bypass Grafting," *Ann. Thorac. Surg.* 63(6 Suppl):S64-S67.
Palcic et al. (1991). "Lung Imaging Fluorescence Endoscope: A Device for Detection of Occult Lung Cancer," *Medical Design and Material*, thirteen pages.
Palcic, B. et al. (1990). "Development of a Lung Imaging Fluorescence Endoscope," *Annual International Conference of the IEEE Engineering in Medicine and Biology Society* 12(1):0196-0197.
Palcic, B. et al. (Aug. 1, 1990). "The Importance of Image Quality for Computing Texture Features in Biomedical Specimens," Proc. SPIE 1205:155-162.
Palcic, B. et al. (Jun. 1, 1991). "Lung Imaging Fluorescence Endoscope: Development and Experimental Prototype," *Proc. SPIE* 1448:113-117.
Palcic, B. et al. (Mar. 1991). "Detection and Localization of Early Lung Cancer by Imaging Techniques," *Chest* 99(3):742-743.
Pandharlpande, P.V. et al. (Mar. 2005). "Perfusion Imaging of the Liver: Current Challenges and Future Goals," *Radiology* 234(3):661-673.
Paques, M. et al. (Mar. 2003). "Axon-Tracing Properties of Indocyanine Green," *Arch Ophthalmol.* 121(3):367-370.
Parungo, C.P. et al. (Apr. 2005). "Intraoperative Identification of Esophageal Sentinel Lymph Nodes with Near-Infrared Fluorescence Imaging," *The Journal of Thoracic and Cardiovascular Surgery* 129(4):844-850.
Parungo, C.P. et al. (Dec. 2004, e-published on Nov. 15, 2004). "In Vivo Optical Imaging of Pleural Space Drainage to Lymph Nodes of Prognostic Significance," *Annals of Surgical Oncology* 11(12):1085-1092.
Peak, M.J. et al. (1986). "DNA-to-Protein Crosslinks and Backbone Breaks Caused by FAR-and NEAR-Ultraviolet and Visible Light Radiations in Mammalian Cells," in *Mechanism of DNA Damage and Repair, Implications for Carcinogenesis and Risk Assessment*, SIMIC, M.G. (ed.) et al., Plenum Press, 233 Spring Street, New York, N.Y. 10013, pp. 193-202.
Peiretti et al. (2005). "Human erythrocyte-ghost-mediated choroidal angiography and photocoagulation." Database Biosis [online] Biosciences Information Service, Philadelphia, PA, US, XP002725023, Database accession No. Prev200600056121 (abstract), three pages.
Peiretti, E. et al. (May 2005). "Human Erythrocyte-Ghost-Mediated Choroidal Angiography and Photocoagulation," *Investigative Ophthalmology & Visual Science*, ARVO Annual Meeting Abstract 46(13):4282, located at <http://iovs.arvojournals.org/article.aspx?articleid=2403707>, last visited on Oct. 7, 2016, two pages.
Perez, M.T. et al. (Sep. 2002). "In Vivo Studies on Mouse Erythrocytes Linked to Transferrin," *IUBMB Life* 54(3):115-121.
Petition for Inter Partes Review of U.S. Pat. No. 8,892,190 (May 11, 2017), filed on by Visionsense Corp., fifty four pages.
Pfister, A.J. et al. (Dec. 1992). "Coronary Artery Bypass Without Cardiopulmonary Bypass," *Ann. Thorac. Surg.* 54(6):1085-1092, (Discussion by S.R. Gundry).
Phillips, R.P. et al. (1991). "Quantification of Diabetic Maculopathy by Digital Imaging of the Fundus," *Eye* 5(1):130-137.
Piermarocchi, S. et al. (Apr. 2002). "Photodynamic Therapy Increases the Eligibility for Feeder Vessel Treatment of Choroidal Neovascularization Caused by Age-Related Macular Degeneration," *American Journal of Ophthalmology* 133(4):572-575.
Profio, A.E. et al. (Jul.-Aug. 1984). "Fluorometer for Endoscopic Diagnosis of Tumors," *Medical Physics* 11(4):516-520.
Profio, A.E. et al. (Jun. 1, 1991). "Endoscopic Fluorescence Detection of Early Lung Cancer," *Proc. SPIE* 1426:44-46.
Profio, A.E. et al. (Nov./Dec. 1979). "Laser Fluorescence Bronchoscope for Localization of Occult Lung Tumors," *Medical Physics* 6:523-525.
Profio, A.E. et al. (Sep.-Oct. 1986). "Digital Background Subtraction for Fluorescence Imaging," *Medical Physics* 13(5):717-721.
Puigdellivol-Sanchez, A. et al. (Apr. 15, 2002). "On the Use of Fast Blue, Fluoro-Gold and Diamidino Yellow for Retrograde Tracing After Peripheral Nerve Injury: Uptake, Fading, Dye Interactions, and Toxicity," *Journal of Neuroscience Methods* 115(2):115-127.

(56) References Cited

OTHER PUBLICATIONS

Pyner, S. et al. (Nov. 2001). "Tracing Functionally Identified Neurones in a Multisynaptic Pathway in the Hamster and Rat Using Herpes Simplex Virus Expressing Green Fluorescent Protein," *Experimental Physiology* 86(6):695-702.

Raabe et al. (2009, e-published on Nov. 12, 2008). "Laser Doppler Imaging for Intraoperative Human Brain Mapping", *NeuroImage* 44:1284-1289.

Raabe, A. et al. (Jan. 2003). "Near-Infrared Indocyanine Green Video Angiography: A New Method for Intraoperative Assessment of Vascular Flow," *Neurosurgery* 52(1):132-139.

Rava, R.P. et al. (Jun. 1, 1991). "Early Detection of Dysplasia in Colon and Bladder Tissue Using Laser-Induced Fluorescence," *Proc. SPIE* 1426:68-78.

Razum, N. et al. (Nov. 1987). "Skin Photosensitivity: Duration and Intensity Following Intravenous Hematoporphyrin Derivatives, HpD and DHE," *Photochemistry and Photobiology* 46(5):925-928.

Report on Observation by C2400-75i and ARGUS20 Under Low illumination conditions, Jan. 17, 2008, six pages.

Request for Invalidation dated Jun. 29, 2007 for Japanese Patent No. JP-3881550, filed by Hamamatsu Photonics, Inc., eighty five pages (with English Translation).

Reuthebuch, O et al. (Feb. 2004). "Novadaq SPY: Intraoperative Quality Assessment in Off Pump Coronary Artery Bypass Grafting," *Chest* 125(2):418-424.

Reuthebuch, O.T. et al. (May 2003). "Graft Occlusion After Deployment of the Symmetry Bypass System," *Ann. Thorac. Surg.* 75(5):1626-1629.

Richards-Kortum, R. et al. (Jun. 1991). "Spectroscopic Diagnosis of Colonic Dysplasia: Spectroscopic Analysis," *Biochemistry and Photobiology* 53(6):777-786.

Roberts, W.W. et al. (Dec. 1997). "Laparoscopic Infrared Imaging," *Surg. Endoscopy* 11(12):1221-1223.

Rodnenkov, O.V. et al. (May 2005). "Erythrocyte Membrane Fluidity and Haemoglobin Haemoporphyrin Conformation: Features Revealed in Patients with Heart Failure," *Pathophysiology* 11(4):209-213.

Ropars, C. (ed.) et al. (1987). *Red Blood Cells as Carriers for Drugs. Potential therapeutic Applications*, Pergamon Press, Oxford, New York, pp. v-vii, (Table of Contents only), four pages.

Ross, G.L. et al. (Dec. 2002). "The Ability of Lymphoscintigraphy to Direct Sentinel Node Biopsy in the Clinically N0 Neck for Patients with Head and Neck Squamous Cell Carcinoma," *The British Journal of Radiology* 75(900):950-958.

Ross, G.L. et al. (Jul. 2004, e-published on Jun. 14, 2000). "Sentinel Node Biopsy in Head and Neck Cancer: Preliminary Results of a Multicenter Trial," *Annals of Surgical Oncology* 11(7):690-696.

Rossi, L. et al. (2001). "Erthrocyte-Mediated Delivery of Dexamethasone in Patients with Chronic Obstructive Pulmonary Disease," *Biotechnol. Appl. Biochem.* 33:85-89.

Rossi, L. et al., "Heterodimer-Loaded RBCs as Bioreactors for Slow Delivery of The Antiviral Drug Azidothymidine and the Antimycobacterial Drug Ethambutol." AIDS Res Hum Retrovir 1999; 15:345-353.

Rossi, L. et al. (2004). "Low Doses of Dexamethasone Constantly Delivered by Autologous Erythrocytes Slow the Progression of Lung Disease in Cystic Fibrosis Patients," *Blood Cells, Molecules, and Diseases* 33:57-63.

Rozen, W.M. et al. (Jan. 2008). "Preoperative Imaging for DIEA Perforator Flaps: A Comparative Study of Computed Tomographic Angiography and Doppler Ultrasound," *Plastic and Reconstructive Surgery* 121(1):9-16. (Per J. Liebes cite with a later OA e-mail dated Mar. 24, 2016).

Rübben, A. et al. (Mar. 1994). "Infrared Videoangiofluorography of the Skin with Indocyanine Green—Rat Random Cutaneous Flap Model and Results in Man," *Microvascular Research* 47(2):240-251.

Rubens, F.D. et al. (2002). "A New and Simplified Method for Coronary and Graft Imaging During CABG," *The Heart Surgery Forum* 5(2):141-144.

Russian Notice of Allowance dated Jul. 29, 2013, issued in counterpart Russian Application No. 2011111078.14, five pages.

Russian Office Action dated Mar. 29, 2013, issued in counterpart Russian Application No. 2011111078.14, three pages.

Sakatani, K. et al. (Nov. 1997). "Noninvasive Optical Imaging of the Subarachnoid Space and Cerebrospinal Fluid Pathways Based on Near Infrared Fluorescence," *J. Neurosurg.* 87(5):738-745.

Salmon, E.D. et al. (Oct. 1994). "High Resolution Multimode Digital Imaging System for Mitosis Studies *In Vivo* and *In Vitro*," *Biol. Bull* 187(2):231-232.

Sato, M. et al., (1991). "Development of a Visualization Method for the Microcirculation of Deep Viscera Using an Infrared Intravital Microscope System," *Research on ME Devices and ME Technology* (with English Translation), five pages.

Satpathy G.R. et al. (Oct. 2004; , e-publication Aug. 7, 2004). "Loading Red Blood Cells with Trehalose: A Step Towards Biostabilization," *Cryobiology* 49(2):123-136.

Schaff, H.V. et al. (Oct. 15, 1996). "Minimal Thoracotomy for Coronary Artery Bypass: Value of Immediate Postprocedure Graft Angiography," *Supplement to Circulation* 94(8):I-51, (Abstract No. 0289), two pages.

Schellingerhout, D. et al. (Oct. 2000). "Quantitation of HSV Mass Distribution in a Rodent Brain Tumor Model," *Gene Therapy* 7(19):1648-1655.

Schmued, L. et al. (Aug. 27, 1990). "In Vivo Anterograde and Retrograde Axonal Transport of the Fluorescent Rhodamine-Dextran-Amine, Fluoro-Ruby, Within the CNS," *Brain Research* 526(1):127-134.

Schmued, L.C. et al. (Oct. 29, 1993). "Intracranial Injection of Fluoro-Gold Results in the Degeneration of Local but not Retrogradely Labeled Neurons," *Brain Research* 626(1-2):71-77.

Schneider Jr., H.C. et al. (Jan. 1975). "Fluorescence of Testicle, An Indication of Viability of Spermatic Cord After Torsion," *Urology* V(1):133-136.

Seeman, P. (Jan. 1, 1967). "Transient Holes in the Erythrocyte Membrane During Hypotonic Hemolysis and Stable Holes in the Membrane After Lysis by Saponin and Lysolecithin," *Journal of Cell Biology* 32(1):55-70.

Sekijima, M. et al. (Sep. 2004). "An Intraoperative Fluorescent Imaging System in Organ Transplantation," *Transplantation Proceedings* 36(7):2188-2190.

Serov, A. et al. (Mar. 1, 2002). "Laser Doppler Perfusion Imaging with a Complimentary Metal Oxide Semiconductor Image Sensor," *Optics Letters* 27(5):300-302.

Serov, A.N. et al. (Sep. 23, 2003). "Quasi-Parallel Laser Doppler Perfusion Imaging Using a CMOS Image Sensor," *Proc. SPIE* 5067:73-84.

Sezgin, M. et al. (Jan. 2004). "Survey Over Image Thresholding Techniques and Quantitative Performance Evaluation," *Journal of Electronic Imaging* 13(1):146-165.

Sherif, A. et al. (Sep. 2001). "Lymphatic Mapping and Detection of Sentinel Nodes in Patients with Bladder Cancer," *The Journal of Urology* 166(3):812-815.

Sheth, S.A. et al. (Apr. 22, 2004). "Linear and Nonlinear Relationships between Neuronal Activity, Oxygen Metabolism, and Hemodynamic Responses," *Neuron* 42(2):347-355.

Shoaib, T. et al. (Jun. 1, 2001). "The Accuracy of Head and Neck Carcinoma Sentinel Lymph Node Biopsy in the Clinically No Neck," *Cancer* 91(11):2077-2083.

Siemers, B.M. et al. (Nov. 2001). "The Acoustic Advantage of Hunting at Low Heights Above Water: Behaviorual Experiments on the European 'Trawling' Bats *Myotis Capaccinii, M Dasycneme and M. Daubentonii*," J. Experimental Biol. 204(Pt. 22):3843-3854.

Skalidis, E.I. et al. (Nov. 16, 2004). "Regional Coronary Flow and Contractile Reserve in Patients with Idiopathic Dilated Cardiomyopathy," *Journal of the American College of Cardiology* 44(10):2027-2032.

Slakter, J.S. et al. (Jun. 1995). "Indocyanine-Green Angiography," *Current Opinion in Ophthalmology* 6(III):25-32.

Smith, G.A. et al. (Mar. 13, 2001). "Herpesviruses Use Bidirectional Fast-Axonal Transport to Spread in Sensory Neurons," *Proceedings of the National Academy of Sciences of the United States of America* 98(6):3466-3470.

(56) References Cited

OTHER PUBLICATIONS

Soltesz, E.G. et al. (Jan. 2005). "Intraoperative Sentinel Lymph Node Mapping of the Lung Using Near-Infrared Fluorescent Quantum Dots," *Ann. Thorac. Surg.* 79(1):269-277.
Sony Corporation. The Sony U-Matic Videocassette Recorder, VO-9800, ten pages.
Staurenghi, G. et al. (Dec. 2001)."Combining Photodynamic Therapy and Feeder Vessel Photocoagulation: A Pilot Study," *Seminars in Ophthalmology* 16(4):233-236.
Stern, M.D. (Mar. 6, 1975). "In Vivo Evaluation of Microcirculation by Coherent Light Scattering," *Nature* 254(5495):56-58.
Still, J. et al. (Mar. 1999). "Evaluation of the Circulation of Reconstructive Flaps Using Laser-Induced Fluorescence of Indocyanine Green," *Ann. Plast. Surg.* 42(3):266-274.
Still, J.M. et al. (Jun. 2001). "Diagnosis of Burn Depth Using Laser-Induced Indocyanine Green Fluorescence: A Preliminary Clinical Trial," *Burns* 27(4):364-371.
Stoeckli, S.J. et al. (Sep. 2001). "Sentinel Lymph Node Evaluation in Squamous Cell Carcinoma of the Head and Neck," *Otolaryngol Head Neck Surg.* 125(3):221-226.
Subramanian, V.A. et al. (Oct. 15, 1995). "Minimally Invasive Coronary Bypass Surgery: A Multi-Center Report of Preliminary Clinical Experience," *Supplement to Circulation* 92(8):I-645, (Abstract No. 3093), two pages.
Sugi, K. et al. (Jan. 2003). "Comparison of Three Tracers for Detecting Sentinel Lymph Nodes in Patients with Clinical N0 Lung Cancer," *Lung Cancer* 39(1):37-40.
Sugimoto, K. et al. (Jun. 2008, e-published on Mar. 19, 2008). "Simultaneous Tracking of Capsid, Tegument, and Envelope Protein Localization in Living Cells Infected With Triply Fluorescent Herpes Simplex Virus 1," *Journal of Virology* 82(11):5198-5211.
Suma, H. et al. (2000). "Coronary Artery Bypass Grafting Without Cardiopulmonary Bypass in 200 Patients," J. Cardiol. 36(2):85-90, (English Abstract only).
Summary of Invention Submitted to EPO, "Development of Novadaq SPY™ Cardiac Imaging Invention," five pages.
Taggart, D.P. et al. (Mar. 2003). "Preliminary Experiences with a Novel Intraoperative Fluorescence Imaging Technique to Evaluate the Patency of Bypass Grafts in Total Arterial Revascularization," *Ann Thorac Surg.* 75(3):870-873.
Taichman, G.C. et al. (Jun. 1987). "The Use of Cardio-Green for Intraoperative Visualization of the Coronary Circulation: Evaluation of Myocardial Toxicity," *Texas Heart Institute Journal* 14(2):133-138.
Takahashi, M. et al. (Sep. 2004). "SPY™: An Innovative Intra-Operative Imaging System to Evaluate Graft Patency During Off-Pump Coronary Artery Bypass Grafting," *Interactive Cardio Vascular and Thoracic Surgery* 3(3):479-483.
Takayama, T. et al. (Apr. 1992). "Intraoperative Coronary Angiography Using Fluorescein Basic Studies and Clinical Application," *Vascular and Endovascular Surgery* 26(3):193-199.
Takayama, T. et al. (Jan. 1991). "Intraoperative Coronary Angiography Using Fluorescein" *The Annals of Thoracic Surgery* 51(1):140-143.
Tanaka, E. et al. (Jul. 2009). "Real-time Assessment of Cardiac Perfusion, Coronary Angiography, and Acute Intravascular Thrombi Using Dual-channel Near-infrared Fluorescence Imaging," *The Journal of Thoracic and Cardiovascular Surgery* 138(1):133-140.
Tang, G.C. et al. (1989). "Spectroscopic Differences between Human Cancer and Normal Lung and Breast Tissues," *Lasers in Surgery and Medicine* 9(3):290-295.
Taylor, K.M. (Apr. 1998). "Brain Damage During Cardiopulmonary Bypass," *Annals of Thoracic Surgery* 65(4):S20-S26.
The American Heritage Medical Dictionary. "Perfuse." p. 401 (2008), three pages.
Thelwall, P.E. et al. (Oct. 2002). "Human Erythrocyte Ghosts: Exploring the Origins of Multiexponential Water Diffusion in a Model Biological Tissue with Magnetic Resonance," *Magnetic Resonance in Medicine* 48(4):649-657.
Torok, B. et al. (May 1996). "Simultaneous Digital Indocyanine Green and Fluorescein Angiography," *Klinische Monatsblatter Fur Augenheilkunde* 208(5):333-336, (Abstract only), two pages.
Translation of Decision of Japanese Patent Office Trial Board revoking Counterpart U.S. Pat. No. 3,881,550, twenty six pages.
Tsutsumi, D. et al. "Moisture Detection of road surface using infrared camera," Reports of the Hokkaido Industrial Research Institute (No. 297), Issued on Nov. 30, 1998, two pages.
Tubbs, R.S. et al. (Apr. 2005). "Anatomic Landmarks for Nerves of the Neck: A Vade Mecum for Neurosurgeons," *Neurosurgery* 56(2 Suppl.):ONS256-ONS260.
U.S. Final Office Action dated Apr. 2, 2013 for U.S. Appl. No. 13/419,368, filed Mar. 13, 2012, five pages.
U.S. Final Office Action dated Apr. 4, 2017 for U.S. Appl. No. 12/933,477, filed Sep. 20, 2010, twelve pages.
U.S. Final Office Action dated Apr. 10, 2008 for U.S. Appl. No. 11/106,154, filed Apr. 14, 2005, six pages.
U.S. Final Office Action dated Apr. 12, 2017 for U.S. Appl. No. 14/543,429, filed Nov. 17, 2014, nine pages.
U.S. Final Office Action dated Apr. 20, 2016 for U.S. Appl. No. 14/543,429, filed Nov. 17, 2014, seven pages.
U.S. Final Office Action dated Apr. 27, 2011 for U.S. Appl. No. 11/515,419, filed Sep. 1, 2006, nine pages.
U.S. Final Office Action dated Aug. 10, 2012 for U.S. Appl. No. 11/912,877, filed Aug. 13, 2008, ten pages.
U.S. Final Office Action dated Dec. 4, 2014 for U.S. Appl. No. 12/776,835, filed May 10, 2010, thirteen pages.
U.S. Final Office Action dated Dec. 31, 2015 for U.S. Appl. No. 14/177,050, filed Feb. 10, 2014, eighteen pages.
U.S. Final Office Action dated Feb. 1, 2013 for U.S. Appl. No. 12/776,835, filed May 10, 2010, thirteen pages.
U.S. Final Office Action dated Feb. 4, 2015 for U.S. Appl. No. 13/314,418, filed Dec. 8, 2011, six pages.
U.S. Final Office Action dated Feb. 13, 2015 for U.S. Appl. No. 14/543,429, filed Nov. 17, 2014, six pages.
U.S. Final Office Action dated Feb. 18, 2010 for U.S. Appl. No. 11/106,154, filed Apr. 14, 2005, six pages.
U.S. Final Office Action dated Jul. 9, 2015 for U.S. Appl. No. 14/543,356, filed Nov. 17, 2014, eight pages.
U.S. Final Office Action dated Jul. 21, 2016 for U.S. Appl. No. 14/543,356, filed Nov. 17, 2014, seven pages.
U.S. Final Office Action dated Jun. 1, 2015 for U.S. Appl. No. 14/543,429, filed Nov. 17, 2014, nine pages.
U.S. Final Office Action dated Jun. 13, 2014 for U.S. Appl. No. 12/776,835, filed May 10, 2010, thirteen pages.
U.S. Final Office Action dated Jun. 25, 2014 for U.S. Appl. No. 12/933,477, filed Sep. 20, 2010, fifteen pages.
U.S. Final Office Action dated Mar. 20, 2017 for U.S. Appl. No. 14/177,050, filed Feb. 10, 2014, twenty three pages.
U.S. Final Office Action dated Mar. 28, 2013 for U.S. Appl. No. 12/063,349, filed May 12, 2010, twenty pages.
U.S. Final Office Action dated May 29, 2013 for U.S. Appl. No. 12/933,477, filed Sep. 20, 2010, twelve pages.
U.S. Final Office Action dated Nov. 6, 2013 for U.S. Appl. No. 13/419,368, filed Mar. 13, 2012, five pages.
U.S. Final Office Action dated Oct. 7, 2011 for U.S. Appl. No. 11/851,312, filed Sep. 6, 2007, ten pages.
U.S. Final Office Action dated Sep. 13, 2011 for U.S. Appl. No. 11/106,154, filed Apr. 14, 2005, five pages.
U.S. Final Office Action dated Sep. 17, 2014 for U.S. Appl. No. 11/515,419, filed Sep. 1, 2006, eleven pages.
U.S. Final Office Action dated Sep. 17, 2015 for U.S. Appl. No. 12/933,477, filed Sep. 20, 2010, six pages.
U.S. Final Office Action dated Sep. 23, 2004 for U.S. Appl. No. 09/744,034, filed Apr. 27, 2001, seven pages.
U.S. Final Office Action dated Sep. 29, 2016 for U.S. Appl. No. 13/922,996, filed Jun. 20, 2013, fourteen pages.
U.S. Non-Final Office Action dated Aug. 6, 2019 for U.S. Appl. No. 15/591,909, filed May 10, 2017, nine pages.
U.S. Non-Final Office Action dated Jul. 23, 2019, for U.S. Appl. No. 15/517,895, thirteen pages.
U.S. Non-Final Office Action dated Apr. 1, 2015 for U.S. Appl. No. 12/933,477, filed Sep. 20, 2010, fourteen pages.

(56) References Cited

OTHER PUBLICATIONS

U.S. Non-Final Office Action dated Apr. 26, 2012 for U.S. Appl. No. 12/776,835, filed May 10, 2010, nine pages.
U.S. Non-Final Office Action dated Apr. 28, 2010 for U.S. Appl. No. 11/946,672, filed Nov. 28, 2007, nine pages.
U.S. Non-Final Office Action dated Aug. 10, 2016 for U.S. Appl. No. 14/177,050, filed Feb. 10, 2014, twenty pages.
U.S. Non-Final Office Action dated Aug. 29, 2014 for U.S. Appl. No. 12/063,349, filed May 12, 2010, nineteen pages.
U.S. Non-Final Office Action dated Dec. 16, 2016 for U.S. Appl. No. 14/868,369, filed Sep. 28, 2015, seven pages.
U.S. Non-Final Office Action dated Dec. 20, 2013 for U.S. Appl. No. 12/933,477, filed Sep. 20, 2010, thirteen pages.
U.S. Non-Final Office Action dated Dec. 30, 2010 for U.S. Appl. No. 11/106,154, filed Apr. 14, 2005, six pages.
U.S. Non-Final Office Action dated Feb. 1, 2011 for U.S. Appl. No. 11/851,312, filed Sep. 6, 2007, seven pages.
U.S. Non-Final Office Action dated Feb. 5, 2016 for U.S. Appl. No. 14/543,356, filed Nov. 17, 2014, seven pages.
U.S. Non-Final Office Action dated Jan. 8, 2018 for U.S. Appl. No. 15/077,677, filed Mar. 22, 2016, nine pages.
U.S. Non-Final Office Action dated Jan. 9, 2009 for U.S. Appl. No. 11/106,154, filed Apr. 14, 2005, six pages.
U.S. Non-Final Office Action dated Jan. 22, 2014 for U.S. Appl. No. 11/851,312, filed Sep. 6, 2007, ten pages.
U.S. Non-Final Office Action dated Jan. 27, 2012 for U.S. Appl. No. 11/912,877, filed Aug. 13, 2008, eleven pages.
U.S. Non-Final Office Action dated Jan. 31, 2018 for U.S. Appl. No. 15/799,727 filed Oct. 31, 2017, seven pages.
U.S. Non-Final Office Action dated Jul. 2, 2015 for U.S. Appl. No. 14/177,050, filed Feb. 10, 2014, nineteen pages.
U.S. Non-Final Office Action dated Jul. 8, 2014 for U.S. Appl. No. 13/314,418, filed Dec. 8, 2011, seven pages.
U.S. Non-Final Office Action dated Jul. 22, 2015 for U.S. Appl. No. 13/314,418, filed Dec. 8, 2011, six pages.
U.S. Non-Final Office Action dated Jun. 11, 2013 for U.S. Appl. No. 11/515,419, filed Sep. 1, 2006, eleven pages.
U.S. Non-Final Office Action dated Jun. 28, 2012 for U.S. Appl. No. 12/063,349, filed May 12, 2010, seventeen pages.
U.S. Non-Final Office Action dated Mar. 6, 2007 for U.S. Appl. No. 11/106,154, filed Apr. 14, 2005, eight pages.
U.S. Non-Final Office Action dated Mar. 10, 2004 for U.S. Appl. No. 09/744,034, filed Apr. 27, 2001, seven pages.
U.S. Non-Final Office Action dated Mar. 13, 2015 for U.S. Appl. No. 14/543,356, filed Nov. 17, 2014, eight pages.
U.S. Non-Final Office Action dated Mar. 22, 2018 for U.S. Appl. No. 15/610,102, filed on May 31, 2017, eleven pages.
U.S. Non-Final Office Action dated Mar. 22, 2019 for U.S. Appl. No. 15/799,727 filed Oct. 31, 2017, eight pages.
U.S. Non-Final Office Action dated May 6, 2015 for U.S. Appl. No. 12/063,349, filed May 12, 2010, seventeen pages.
U.S. Non-Final Office Action dated May 21, 2015 for U.S. Appl. No. 13/922,996, filed Jun. 20, 2013, fourteen pages.
U.S. Non-Final Office Action dated Nov. 9, 2015 for U.S. Appl. No. 14/177,045, filed Feb. 10, 2014, seven pages.
U.S. Non-Final Office Action dated Nov. 18, 2016 for U.S. Appl. No. 12/933,477, filed Sep. 20, 2010, six pages.
U.S. Non-Final Office Action dated Nov. 27, 2015 for U.S. Appl. No. 14/543,429, filed Nov. 17, 2014, six pages.
U.S. Non-Final Office Action dated Oct. 3, 2013 for U.S. Appl. No. 12/776,835, filed May 10, 2010, twelve pages.
U.S. Non-Final Office Action dated Oct. 12, 2016 for U.S. Appl. No. 14/543,429, filed Nov. 17, 2014, nine pages.
U.S. Non-Final Office Action dated Oct. 13, 2017 for U.S. Appl. No. 13/922,996, filed Jun. 20, 2013, seventeen pages.
U.S. Non-Final Office Action dated Oct. 26, 2017 for U.S. Appl. No. 14/543,429, filed Nov. 17, 2014, nine pages.
U.S. Non-Final Office Action dated Oct. 28, 2016 for U.S. Appl. No. 14/543,356, filed Nov. 17, 2014, eight pages.
U.S. Non-Final Office Action dated Sep. 5, 2012 for U.S. Appl. No. 12/933,477, filed Sep. 20, 2010, seven pages.
U.S. Non-Final Office Action dated Sep. 15, 2010 for U.S. Appl. No. 11/106,154, filed Apr. 14, 2005, six pages.
U.S. Non-Final Office Action dated Sep. 27, 2017 for U.S. Appl. No. 14/177,050, filed Feb. 10, 2014, twenty two pages.
U.S. Non-Final Office Action dated Sep. 30, 2010 for U.S. Appl. No. 11/515,419, filed Sep. 1, 2006, eleven pages.
U.S. Notice of Allowance dated Jul. 16, 2019, for U.S. Appl. No. 12/776,835, filed May 10, 2010, seven pages.
U.S. Notice of Allowance dated Apr. 17, 2014 for U.S. Appl. No. 13/419,368, filed Mar. 13, 2012, five pages.
U.S. Notice of Allowance dated Aug. 7, 2014 for U.S. Appl. No. 13/850,063, filed Mar. 25, 2013, nine pages.
U.S. Notice of Allowance dated Dec. 2, 2016 for U.S. Appl. No. 14/598,832, filed Jan. 16, 2015, seven pages.
U.S. Notice of Allowance dated Dec. 4, 2018 for U.S. Appl. No. 11/515,419, filed Sep. 1, 2006, seven pages.
U.S. Notice of Allowance dated Dec. 6, 2017 for U.S. Appl. No. 15/476,290, filed Mar. 31, 2017, nine pages.
U.S. Notice of Allowance dated Dec. 18, 2018 for U.S. Appl. No. 13/922,996, filed Jun. 20, 2013, six pages.
U.S. Notice of Allowance dated Jan. 10, 2019 for U.S. Appl. No. 15/610,102, filed May 31, 2017, five pages.
U.S. Notice of Allowance dated Jul. 12, 2017 for U.S. Appl. No. 14/868,369, filed Sep. 28, 2015, nine pages.
U.S. Notice of Allowance dated Jul. 13, 2016 for U.S. Appl. No. 14/598,832, filed Jan. 16, 2015, seven pages.
U.S. Notice of Allowance dated Jun. 15, 2018 for U.S. Appl. No. 11/515,419, filed Sep. 1, 2006, five pages.
U.S. Notice of Allowance dated Mar. 7, 2005 for U.S. Appl. No. 09/744,034, filed Apr. 27, 2001, five pages.
U.S. Notice of Allowance dated Mar. 15, 2016 for U.S. Appl. No. 14/598,832, filed Jan. 16, 2015, seven pages.
U.S. Notice of Allowance dated Mar. 29, 2018 for U.S. Appl. No. 14/177,050, filed Feb. 10, 2014, ten pages.
U.S. Notice of Allowance dated May 15, 2019 for U.S. Appl. No. 15/610,102, filed May 31, 2017, eight pages.
U.S. Notice of Allowance dated May 26, 2016 for U.S. Appl. No. 14/177,045, filed Feb. 10, 2014, eight pages.
U.S. Notice of Allowance dated Nov. 25, 2015 for U.S. Appl. No. 14/598,832, filed Jan. 16, 2015, seven pages.
U.S. Notice of Allowance dated Nov. 30, 2010 for U.S. Appl. No. 11/946,672, filed Nov. 28, 2007, six pages.
U.S. Notice of Allowance dated Oct. 4, 2013 for U.S. Appl. No. 11/912,877, filed Aug. 13, 2008, nine pages.
U.S. Notice of Allowance dated Oct. 6, 2014 for U.S. Appl. No. 13/419,368, filed Mar. 13, 2012, five pages.
U.S. Notice of Allowance dated Oct. 16, 2014 for U.S. Appl. No. 13/850,063, filed Mar. 25, 2013, eight pages.
U.S. Notice of Allowance dated Oct. 17, 2018 for U.S. Appl. No. 12/933,477, filed Sep. 20, 2010, seven pages.
U.S. Notice of Allowance dated Oct. 18, 2012 for U.S. Appl. No. 12/841,659, filed Jul. 22, 2010, seven pages.
U.S. Notice of Allowance dated Oct. 29, 2018 for U.S. Appl. No. 12/063,349, filed May 12, 2010, eight pages.
U.S. Notice of Allowance dated Sep. 6, 2018 for U.S. Appl. No. 12/776,835, filed May 10, 2010, five pages.
U.S. Notice of Allowance dated Sep. 6, 2018 for U.S. Appl. No. 13/922,996, filed Jun. 20, 2013, nine pages.
U.S. Notice of Allowance dated Sep. 11, 2018 for U.S. Appl. No. 15/799,727, filed Oct. 31, 2017, eight pages.
U.S. Notice of Allowance dated Sep. 26, 2018 for U.S. Appl. No. 15/610,102, filed May 31, 2017, eight pages.
U.S. Notice of Allowance dated Jul. 10, 2019 for U.S. Appl. No. 15/799,727, filed Oct. 31, 2017, seven pages.
U.S. Appl. No. 16/291,930, filed Mar. 4, 2019. (Copy not submitted herewith pursuant to the waiver of 37 C.F.R. §1.98(a)(2)(iii) issued by the Office dated Sep. 21, 2004).
U.S. Appl. No. 16/356,766, filed Mar. 18, 2019. (Copy not submitted herewith pursuant to the waiver of 37 C.F.R. §1.98(a)(2)(iii) issued by the Office dated Sep. 21, 2004).

(56) References Cited

OTHER PUBLICATIONS

U.S. Restriction Requirement dated Jan. 17, 2019 for U.S. Appl. No. 15/591,909, filed May 10, 2017, seven pages.
U.S. Restriction Requirement dated Jun. 26, 2017 for U.S. Appl. No. 15/077,677, filed Mar. 22, 2016, seven pages.
Unno, N. et al. (Feb. 2008, e-published on Oct. 26, 2007). "Indocyanine Green Fluorescence Angiography for intraoperative assessment of Blood flow: A Feasibility Study," *Eur J Vasc Endovasc Surg.* 35(2):205-207.
Uren, R.F. (Jan. 2004). "Cancer Surgery Joins the Dots," *Nature Biotechnology* 22(1):38-39.
Valero-Cabré, A. et al. (Jan. 15, 2001). "Superior Muscle Reinnervation after Autologous Nerve Graft or Poly-L-Lactide-∈-Caprolactone (PLC) Tube Implantation in Comparison to Silicone Tube Repair," *Journal of Neuroscience Research* 63(2):214-223.
Van Son, J.A.M. et al. (Nov. 1997). "Thermal Coronary Angiography for Intraoperative Testing of Coronary Patency in Congenital Heart Defects," *Ann Thorac Surg.* 64(5):1499-1500.
Verbeek, X. et al. (2001). "High-Resolution Functional Imaging With Ultrasound Contrast Agents Based on RF Processing in an In Vivo Kidney Experiment", *Ultrasound in Med. & Biol.* 27(2):223-233.
Wachi, A. et al. (Apr. 1995). "Characteristics of Cerebrospinal Fluid Circulation in Infants as Detected With MR Velocity Imaging," *Child's Nery Syst* 11(4):227-230.
Wagnieres, G.A. et al. (Jul. 1, 1990). "Photodetection of Early Cancer by Laser Induced Fluorescence of a Tumor-Selective Dye: Apparatus Design and Realization," *Proc. SPIE* 1203:43-52.
Weinbeer, M. et al. (Nov. 25, 2013). "Behavioral Flexibility of the Trawling Long-Legged Bat, Macrophyllum Macrophyllum (Phyllostomidae)," *Frontiers in Physiology* 4(Article 342):1-11.
What is Perfusion? A Summary of Different Typed of Perfusion. (Sep. 1, 2004). Located at, <http://www.perfusion.com/cgi-bin/absolutenm/templates/articledisplay.asp?articleid=1548#.Vo8Hv02FPGj>, last visited on Jan. 7, 2016, two pages.
Wise, R.G. et al. (Nov. 2005). "Simultaneous Measurement of Blood and Myocardial Velocity in the Rat Heart by Phase Contrast MRI Using Sparse q-Space Sampling" *Journal of Magnetic Resonance Imaging* 22(5):614-627.
Woitzik, J. et al. (Apr. 2005). "Intraoperative Control of Extracranial-Intracranial Bypass Patency by Near-Infrared Indocyanine Green Videoangiography," *J. Neurosurg.* 102(4):692-698.
Wollert, H.G. et al. (Dec. 1989). "Intraoperative Visualization of Coronary Artery Fistula Using Medical Dye," *The Thoracic and Cardiovascular Surg.* 46(6):382-383.
Written Opinion of the International Searching Authority dated Dec. 3, 2009 for PCT Patent Application No. PCT/IB2009/005700, filed on Apr. 14, 2009, six pages.
Written Opinion of the International Searching Authority dated Dec. 3, 2015 for PCT Patent Application No. PCT/CA2015/050973 filed on Sep. 28, 2015, five pages.
Written Opinion of the International Searching Authority dated Feb. 1, 2012 for PCT Patent Application No. PCT/IB2011/002381, filed on Sep. 20, 2011, four pages.
Written Opinion of the International Searching Authority dated Jan. 22, 2014 for PCT Patent Application No. PCT/162013/001934, filed on Jun. 20, 2013, six pages.
Written Opinion of the International Searching Authority dated Jul. 4, 2008 for PCT Patent Application No. PCT/US2007/080847, filed on Oct. 9, 2007, six pages.
Written Opinion of the International Searching Authority dated Jun. 2, 2009 forPCT Patent Application No. PCT/EP2008/008547, filed on Oct. 9, 2008, eleven pages.
Written Opinion of the International Searching Authority dated Jun. 8, 2009 for PCT Patent Application No. PCT/CA2009/000073, filed on Jan. 23, 2009, four pages.
Wu, C. et al. (Apr. 15, 2005). "cGMP (Guanosine 3',5'—Cyclic Monophosphate) Transport Across Human Erythrocyte Membranes," *Biochemical Pharmacology* 69(8):1257-1262.
Yada, T. et al. (May 1993). "In Vivo Observation of Subendocardial Microvessels of the Beating Porcine Heart Using a Needle-Probe Videomicroscope with a CCD Camera," *Circulation Research* 72(5):939-946.
Yamaguchi, S. et al. (Apr. 2005). "Evaluation of Skin Perfusion After Nipple-Sparing Mastectomy by Indocyanine Green Dye" *Journal of Saitama Medical University, Japan,* 32(2):45-50, (With English Abstract).
Yoneya, S. et al. (Jun. 1998). "Binding Properties of Indocyanine Green in Human Blood," *IOVS* 39(7):1286-1290.
Yoneya, S. et al. (Sep. 1993). "Improved Visualization of the Choroidal Circulation with Indocyanine Green Angiography," *Arch Opthalmol.* 111(9):1165-1166.
Young. I.T. et al. (1993). "Depth of Focus in Microscopy," SCIA '93, Proc. of the 8th Scandinavian Conference on Image Analysis, Tromso, Norway, pp. 493-498, six pages.

\* cited by examiner

Red and Infrared Diodes

QUANTIFICATION OF ABSOLUTE BLOOD FLOW IN TISSUE USING FLUORESCENCE-MEDIATED PHOTOPLETHYSMOGRAPHY

REFERENCE TO RELATED APPLICATIONS

This application is a national stage application under 35 USC 371 of International Application No. PCT/IB2014/065189, filed Oct. 9, 2014, the entire contents of which are incorporated herein by reference.

TECHNICAL FIELD OF THE INVENTION

The present invention relates generally to the field of optical assessment of blood flow in tissue using photoplethysmography (PPG), and in particular to the quantitative assessment of blood flow in tissue, including microvascular blood flow in tissue.

BACKGROUND OF THE INVENTION

Perfusion refers to the flow of blood into and out of the tissue capillary bed. Quantification of tissue perfusion is of interest to clinicians across many surgical and non-surgical specialties. Although simple binary assessment (flow versus no-flow) may be adequate for some clinical applications, quantification of perfusion in standard measures is desirable in many other clinical applications. To date, quantitative assessment of tissue perfusion has remained elusive.

Photoplethysmography (PPG) is an optical technique that can be used to estimate changes in microvascular blood volume, and PPG-based technology has been deployed in commercially available medical devices for assessing pulse rate, oxygen saturation, blood pressure, and cardiac output. A typical output of such devices is the PPG waveform that corresponds to the heartbeat of the subject. Despite the relatively wide application of PPG technology to such medical devices, PPG has not been utilized to provide measurements in standardized units when assessing blood flow. A PPG technology with such capabilities would enable routine measurements of blood flow in tissue, including perfusion measurements, to be made in standardized units of volume/unit time/tissue area. This would be of significant value to clinicians, as such measurements would allow direct inter-site and inter-subject comparisons.

SUMMARY OF THE INVENTION

In accordance with a first aspect of the invention, there is provided a method for measuring a time-varying change in an amount of blood in a tissue volume. The method includes exciting a fluorescence agent in the blood, such as for example indocyanine green (ICG), acquiring a time-varying light intensity signal during a pulsatile flow of the blood through the tissue volume, wherein the pulsatile flow has a diastolic and a systolic phase resembling a conventional photoplethysmogram, and processing the acquired time-varying light intensity signal to obtain a measurement of the time-varying change in the amount of blood in the tissue volume.

In the first aspect, the method may exclude any step of administering the fluorescence agent to a subject.

Furthermore, in the first aspect, the method may exclude correlating the measurement of the time-varying change in the amount of blood in the tissue volume to a physiological parameter, a diagnostic parameter, or a pathological parameter.

In accordance with a second aspect, there is provided an apparatus for measuring a time-varying change in an amount of blood in a tissue volume. The apparatus includes means for exciting a fluorescence agent in the blood, such as for example ICG, means for acquiring a time-varying light intensity signal during a pulsatile flow of the blood through the tissue volume, wherein the pulsatile flow has a diastolic and a systolic phase resembling a conventional photoplethysmogram, and means for processing the acquired time-varying light intensity signal to obtain a measurement of the time-varying change in the amount of blood in the tissue volume.

In a third aspect, there is provided a kit for measuring a time-varying change in an amount of blood in a tissue volume, the kit including the apparatus of the second aspect and a fluorescence agent such as, for example, ICG.

In a fourth aspect, there is provided a fluorescence agent for use in a method for measuring a time-varying change in an amount of blood in a tissue volume of a subject, the method being according to the first aspect.

In the various aspects of the present invention, a modified Beer Lambert law is applied at the diastolic and systolic phases of the pulsatile flow of blood through tissue volume such that:

$$\Delta L = \ln[(I_e\Phi - I_m/I_e\Phi - I_p)](\varepsilon C)^{-1}$$

where $\Delta L$ is a change in aggregate blood layer thickness within a given tissue volume, $I_e$ is an intensity of an excitation light exciting the fluorescence agent in the blood, $\Phi$ is a quantum efficiency of the fluorescence agent, $I_m$ is an intensity of the time-varying light intensity signal during the diastolic phase minimum of the pulsatile flow of the blood through the tissue volume, $I_p$ is an intensity of the time-varying light intensity signal during the systolic phase maximum of the pulsatile flow of the blood through the tissue volume, $\varepsilon$ is a molar absorption coefficient for the fluorescence agent, and C is an instantaneous molar concentration of the fluorescence agent in the blood.

In the various aspects of the present invention, the instantaneous molar concentration of the fluorescence agent in the blood is preferably determined by utilizing a concentration-mediated change in a fluorescence emission spectrum of the fluorescence agent. The concentration-mediated change in fluorescence emission spectrum of the fluorescence agent includes a monotonic spectral shift.

In various aspects of the present invention, utilizing the concentration-mediated change in fluorescence emission spectrum of the fluorescence agent preferably includes selecting first and second spectral bands of fluorescence emission spectrum of the fluorescence agent, acquiring first and second intensities of fluorescence emission integrated over wavelengths in the first and second spectral bands respectively, calculating a ratio of the first and second intensities, and deriving a value for C from the ratio. In various embodiments, the first spectral band includes wavelengths ranging from about 780 nm to about 835 nm, or a subset thereof, and the second spectral band includes wavelengths ranging from about 835 nm to about 1000 nm, or a subset thereof.

According to an embodiment, the first and second spectral bands are selected such that one of the first and second intensities varies monotonically with C, and one of the first and second intensities is unchanged with C. In another embodiment, the first and second spectral bands are selected such that the first and second intensities increase monotonically with C, but at different rates. In yet further embodiment, the first and second spectral bands are selected such that the first intensity increases monotonically with C, and the second intensity decreases monotonically with C. The instantaneous molar concentration of the fluorescence agent in blood ranges in various embodiments from about 2 μM to about 10 mM.

The optional features of the invention set out above may be applied, in any combination, with any aspect of the invention, unless the context demands otherwise.

Further optional features of the invention are set out below.

BRIEF DESCRIPTION OF THE DRAWINGS

In accompanying drawings which illustrate embodiments of the invention.

DETAILED DESCRIPTION OF THE INVENTION

Reference will now be made in detail to implementations and embodiments of various aspects and variations of the invention, examples of which are illustrated in the accompanying drawings.

Figure 1:
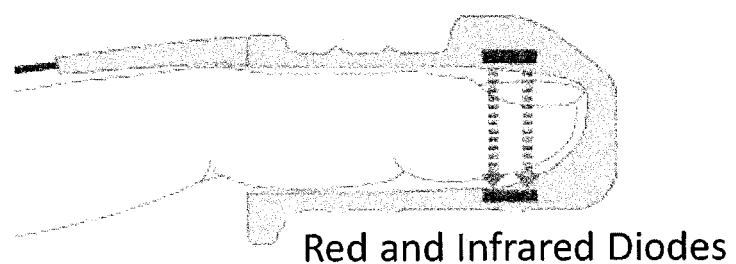
FIG. 1 schematically illustrates the use of conventional photoplethysmography (PPG) in which a fingertip sensor is used to measure pulse rate, blood oxygen saturation or both.
Figure 1:
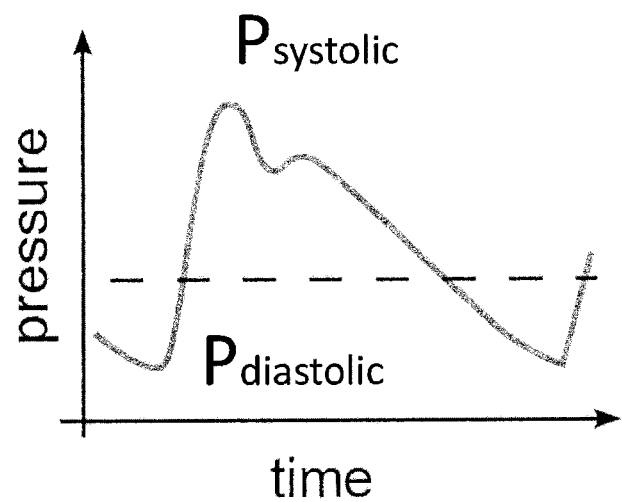

Conventional photoplethysmography (PPG) can estimate changes in tissue blood volume by detecting changes in the amount of red or near-infrared light transmitted through the tissue. As the blood volume within tissue expands and contracts during a cardiovascular pressure pulse corresponding to the heartbeat of the subject, the amount of light absorbed by the blood volume increases and decreases, respectively. As shown in FIG. 1, for example, the aggregate blood volume in the fingertip blood vessels is smallest during cardiovascular pressure pulse diastole and the volume is greatest during systole. Although it may be used for measuring pulse rate and blood oxygenation, this application of PPG technology is not configured to provide volumetric flow measurements in standardized units.

To be able to provide volumetric microvascular blood flow measurements in standardized units, the metrics of the PPG waveform must be related in a known and repeatable fashion to the blood volume changes in the tissue. It is possible to establish this type of deterministic relationship with the application of a modified Beer-Lambert law (also known as Beer's law, or the Beer-Lambert-Bouguer law). The Beer-Lambert law relates the attenuation of a light beam passing through a medium to the path length through the medium and its absorptivity and this relationship utilized in conventional PPG. Conventional PPG is performed by passing a beam of near-IR wavelengths of light through tissue (e.g., a fingertip), but the need for trans-illumination of tissue significantly limits application of this method to the more general case of volumetric blood flow measurements in tissue. According to an embodiment, the present invention utilizes a modified Beer-Lambert law to enable such blood flow measurements using fluorescent light wavelengths emitted by a fluorescence agent such as a fluorescence dye. Such a dye may, for example, be bound preferentially to blood plasma, thereby making it possible to position both the light beam source and fluorescent light detector on the surface of the tissue. The fluorescent light emitted from, for example, the dye-tagged plasma component of blood will conform to the modified Beer-Lambert law and, by solving the equation for the optical path length and quantifying the respective parameters, fluorescence-mediated PPG is capable of providing volumetric blood flow measurements, including microvascular blood flow measurements without trans-illumination.

Thus, in contrast to the conventional PPG technology, the present invention provides fluorescence-mediated photoplethysmography (FM-PPG) for measuring time-varying changes in the amount of blood in a tissue volume, and presenting these changes as a blood flow, including microvascular blood flow, in standardized units (e.g., volume/unit time). With FM-PPG, according to the various embodiments, the detected fluorescence intensity is proportional to the instantaneous concentration of a fluorescence agent in the blood (e.g., a fluorescence agent in the blood plasma), and can thus be utilized to determine blood flow in tissue, including microvascular blood flow or perfusion. Blood flow in tissue is generally understood as an increase in the total amount of blood flowing into an anatomic structure or region; blood flow encompasses tissue perfusion or microvascular blood flow, which is the amount of blood flowing through the capillaries of the vascular bed of the anatomic structure or region. In various embodiments, the method and apparatus of the present invention are used for measuring blood flow in tissue, and more particularly, for measuring perfusion or microvascular blood flow in tissue. In various embodiments, the use of the method and apparatus of the present invention includes the ability to discriminate between the blood flow and the microvascular blood flow.

In accordance with one aspect of the invention, there is provided a method for measuring a time-varying change in an amount of blood in a tissue volume. The method comprises exciting a fluorescence agent in the blood, acquiring a time-varying light intensity signal, which includes a time-varying fluorescence intensity signal, during a pulsatile flow of the blood through the tissue volume, the pulsatile flow having a diastolic phase and a systolic phase resembling a conventional photoplethysmogram. The method further comprises processing the acquired time-varying light intensity signal to obtain a measurement of the time-varying change in the amount of blood in the tissue volume by applying a modified Beer-Lambert law at the diastolic and systolic phases.

In various embodiments, a suitable fluorescence agent is an agent which can circulate with the blood (e.g., an agent which can circulate with, for example a component of the blood such as plasma in the blood) and which fluoresces when exposed to appropriate excitation light energy. Furthermore, the fluorescence agent exhibits a concentration-mediated change in its fluorescence emission spectrum. In various embodiments, the concentration-mediated change includes a monotonic spectral shift in the fluorescence emission spectrum of the fluorescence agent. An example of the fluorescence agent is a fluorescence dye, which includes any non-toxic fluorescence dye exhibiting a monotonic spectral shift with concentration. In certain embodiments, the fluorescence dye is a dye that emits light in the near-infrared spectrum. In certain embodiments, the fluorescence dye is a tricarbocyanine dye such as, for example, indocyanine green (ICG). In other embodiments the fluorescence dye may further be or comprise fluorescein isothiocyanate, rhodamine, phycoerythrin, phycocyanin, allophycocyanin, o-phthaldehyde, fluorescamine, rose Bengal, trypan blue, fluoro-gold, or a combination thereof, using excitation light wavelengths appropriate to each dye. In some embodiments, an analogue or a derivative of the fluorescence dye may be used. For example, a fluorescence dye analog or a derivative includes a fluorescence dye that has been chemically modified, but still retains its ability to fluoresce when exposed to light energy of an appropriate wavelength.

One aspect of the method of measuring the time-varying change in the amount of blood in the tissue volume of the subject comprises administering the fluorescence agent to the subject such that the fluorescence agent circulates with the blood in the tissue volume as the blood flows through the tissue volume. In various embodiments, the fluorescence agent may be administered to the subject intravenously, e.g., as a bolus injection, in a suitable concentration for imaging. In various embodiments, the fluorescence agent may be injected into a vein, artery, microvasculature (e.g., a capillary bed) or a combination thereof of the subject such that it circulates in the microvasculature. In embodiments in which multiple fluorescence agents are used, such agents may be administered simultaneously, e.g. in a single bolus, or sequentially, e.g. in separate boluses. In some embodiments, the fluorescence agent may be administered by a catheter. In certain embodiments, the fluorescence agent may be administered to the subject less than an hour in advance of performing the measurement according to the various embodiments. For example, the fluorescence agent may be administered to the subject less than 30 minutes in advance of the measurement. In yet other embodiments, the fluorescence agent may be administered at least 30 seconds in advance of performing the measurement. In still other embodiments, the fluorescence agent may be administered contemporaneously with performing the measurement as described in connection with the various embodiments.

In another aspect, the method may exclude any step of administering the fluorescence agent to the subject.

The fluorescence agent may be provided as a lyophilized powder, solid, or liquid. In certain embodiments, the fluorescence agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence agent may be reconstituted with water immediately before administration. In various embodiments, any diluent or carrier which will maintain the fluorescence agent in solution may be used. As an example, in certain embodiments where the fluorescence agent is ICG, it may be reconstituted with water. In some embodiments, once the fluorescence agent is reconstituted, it may be mixed with additional diluents and carriers. In some embodiments, the fluorescence agent may be conjugated to another molecule, e.g., a protein, a peptide, an amino acid, a synthetic polymer, or a sugar e.g., to enhance solubility, stability, imaging properties or a combination thereof. Additional buffering agents may optionally be added including Tris, HCl, NaOH, phosphate buffer, HEPES.

In various embodiments, the fluorescence agent may be administered in various concentrations to achieve a desired circulating concentration in the blood. For example, when the fluorescence agent is ICG, it may be administered at a concentration of about 2.5 mg/mL to achieve a circulating concentration of about 5 µM to about 10 µM in blood. In various embodiments, the upper concentration limit for the administration of the fluorescence agent is the concentration at which the fluorescence agent becomes clinically toxic in circulating blood, and the lower concentration limit is the instrumental detection limit for detecting the fluorescence agent in circulating blood. In various other embodiments, the upper concentration limit for the administration of the fluorescence agent is the concentration at which the fluorescence agent becomes self-quenching. In further embodiments, a lower concentration limit for the administration of the fluorescence agent is the concentration at which the fluorescence agent becomes too difficult for conventional imaging technology to detect. For example, when the fluorescence agent is ICG, the circulating concentration of the fluorescence agent may range from 2 µM to about 10 mM.

The method for measuring the time-varying change in the amount of blood in the tissue volume further comprises acquiring the time-varying light intensity signal during the pulsatile flow of the blood through the tissue volume. In various embodiments, the pulsatile flow arises from a cardiovascular pressure pulse, which may be generated by a heartbeat or simulated heartbeat (e.g., by using a blood pump). The pulsatile flow comprises a diastolic phase and a systolic phase. Furthermore, the diastolic and systolic phases resemble a conventional photoplethysmogram.

The method yet further comprises processing the acquired time-varying light intensity signal (e.g., a time-varying fluorescent light intensity signal) to provide a measurement of the time-varying change in the amount of blood in the tissue volume wherein a modified Beer-Lambert law is applied at the diastolic and systolic phases. The modified Beer-Lambert law for emitted fluorescent light may be written as:

$$\Delta L = \ln[(I_e\Phi - I_m/I_e\Phi - I_p)](\varepsilon C)^{-1}$$

wherein $\Delta L$ is a change in aggregate blood layer thickness within a given tissue volume, $I_e$ is an intensity of an excitation light exciting the fluorescence agent, $\Phi$ is a quantum efficiency of the fluorescence agent, $I_m$ is an intensity of the time-varying light intensity signal during the diastolic phase minimum of the pulsatile flow of the blood through the tissue volume, $I_p$ is an intensity of the time-varying light intensity signal during the systolic phase maximum of the pulsatile flow of the blood through the tissue volume, is a molar absorption coefficient for the fluorescence agent, and C is an instantaneous molar concentration of the fluorescence agent in the blood.

Figure 2:
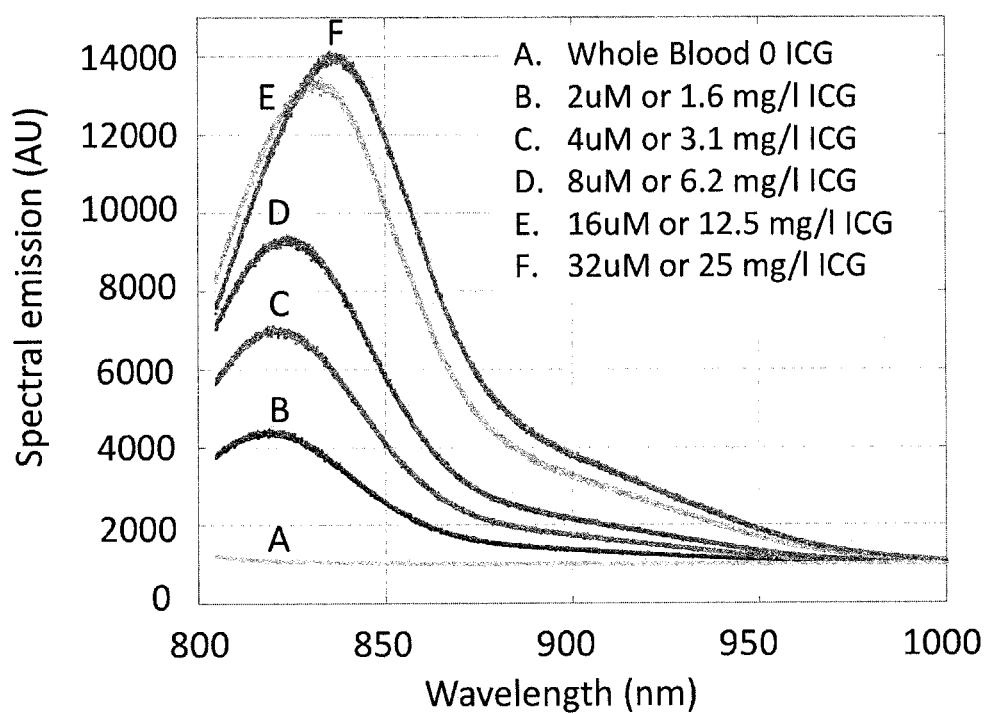
FIG. 2 shows fluorescence emission spectra of indocyanine green (ICG) dye shifting to longer wavelengths with increasing molar concentration of the dye in blood according to an embodiment.

As demonstrated in FIG. 2, the emission spectrum for ICG dye in whole blood is different for each different molar concentration of the dye. In various embodiments, the instantaneous molar concentration of the fluorescence agent is determined by utilizing a concentration-mediated change in a fluorescence emission spectrum of the fluorescence agent. The concentration-mediated change includes a monotonic spectral shift in the fluorescence emission spectrum of the fluorescence agent.

Figure 3:
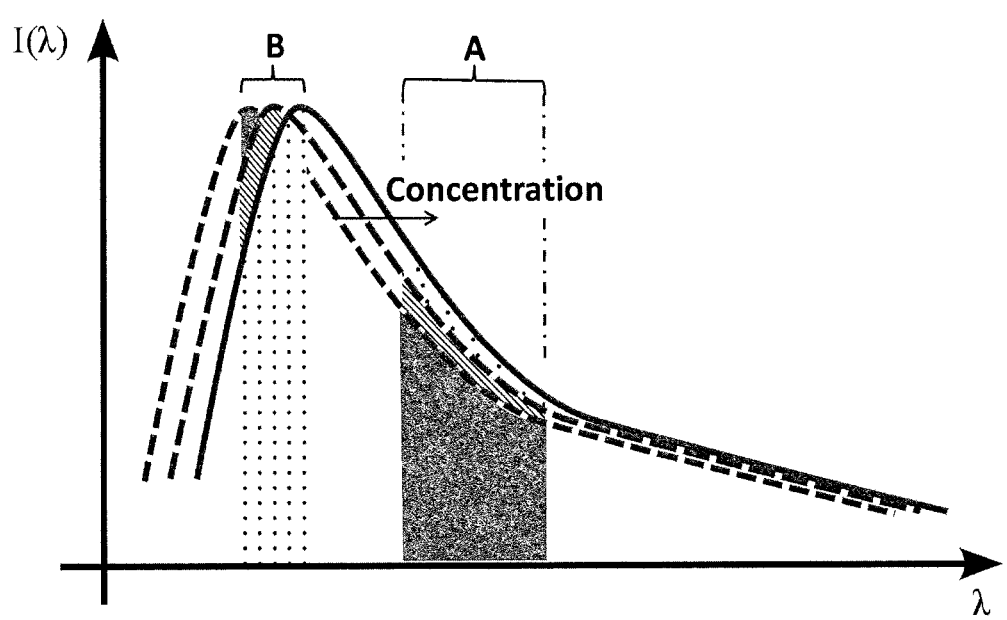
FIG. 3 illustrates an embodiment in which an instantaneous molar concentration of the fluorescence agent in the blood is determined by utilizing a spectral shift in the fluorescence emission spectrum of the fluorescence agent where first and second spectral bands are selected such that one of the first and second intensities varies monotonically with concentration, and one of the first and second intensities is unchanged with concentration.

In various embodiments, utilizing the concentration-mediated change in the fluorescence emission spectrum of the fluorescence agent comprises selecting first and second spectral bands of a fluorescence emission spectrum of the fluorescence agent (e.g., as is shown in FIG. 3), acquiring first and second intensities of fluorescence emission integrated over wavelengths in the first and second spectral bands respectively, calculating a ratio of the first and second intensities, and deriving a value for C in the modified Beer-Lambert law from the calculated ratio.

In various embodiments, the first and second spectral bands may be selected in a number of ways. According to an embodiment, the first and second spectral bands are selected such that one of the first and second intensities varies (increases or decreases) monotonically with C, and one of the first and second intensities is unchanged with C. For example, as is illustrated in FIG. 3, the intensity of fluorescence emission integrated over wavelengths for any bands selected in range B will remain nominally unchanged with increasing concentration of the fluorescence agent. Furthermore, the intensity of fluorescence emission integrated over wavelengths for any bands selected in range A will decrease with C. Consequently, the ratio of intensities of bands from A/B will decrease with C.

Figure 4:
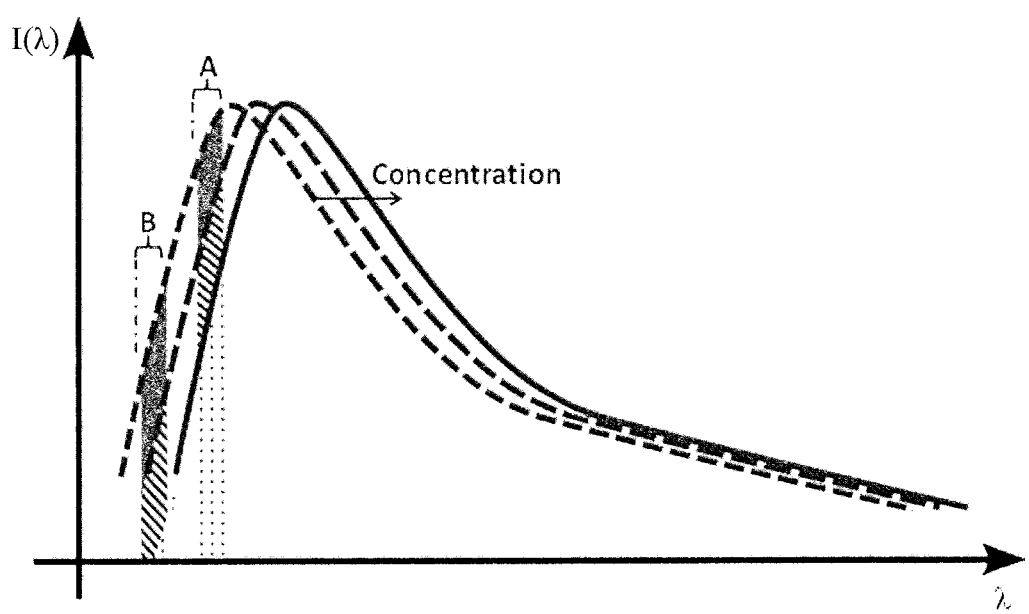
FIG. 4 illustrates an embodiment in which an instantaneous molar concentration of the fluorescence agent in the blood is determined by utilizing a spectral shift in the fluorescence emission spectrum of the fluorescence agent where first and second spectral bands are selected such that the first and second intensities increase monotonically with concentration, but at different rates.

According to another embodiment, the first and second spectral bands are selected such that the first and second intensities decrease monotonically with C, but at different rates. For example, as is illustrated in FIG. 4, the intensity of fluorescence emission integrated over wavelengths for any bands selected in range B will decrease with C, but the intensity of fluorescence emission integrated over wavelengths for any bands selected in range A will decrease more slowly with C. Consequently, the ratio of intensities of bands from A/B will decrease with C.

Figure 5:
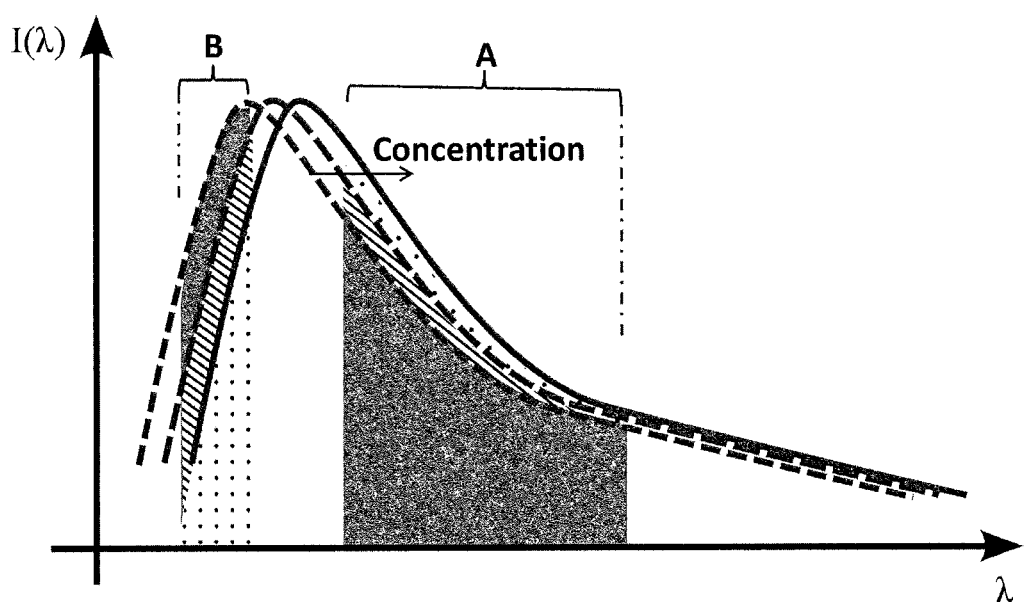
FIG. 5 illustrates an embodiment in which an instantaneous molar concentration of the fluorescence agent in the blood is determined by utilizing a spectral shift in the fluorescence emission spectrum of the fluorescence agent where first and second spectral bands are selected such that the first intensity increases monotonically with concentration, and the second intensity decreases monotonically with concentration.

According to yet another embodiment, the first and second spectral bands are selected such that the first intensity increases monotonically with C, and the second intensity decreases monotonically with C. For example, as is illustrated in FIG. 5, the intensity of fluorescence emission integrated over wavelengths for any bands selected in range B will increase with C, but the intensity of fluorescence emission integrated over wavelengths for any bands selected in range A will decrease with C. Consequently, the ratio of intensities of bands from A/B will decrease with C, but will do so at a greater rate than in the previous embodiments.

In various embodiments, the first spectral band comprises wavelengths ranging from about 780 nm to about 835 nm, or a subset thereof, and the second spectral band comprises wavelengths ranging from about 835 nm to about 1000 nm, or a subset thereof when, for example, the fluorescence agent is ICG.

By selecting the first and second spectral bands as described in connection with the various embodiments, a clinically discernible variation in the ratio is achieved over the range of clinically anticipated concentrations of the fluorescence agent in the circulating blood, and thus the instantaneous molar concentration, C, of the fluorescence agent can be determined.

In various embodiments, the method may further comprise correlating the measurement of the time-varying change in the amount of blood in the tissue volume to a biological parameter, a physiological parameter, a diagnostic parameter, a pathological parameter or a combination thereof. In an alternative embodiment, the method may comprise deriving a measurement of a change in a biological parameter, a physiological parameter, a diagnostic parameter, a pathological parameter or a combination thereof from the measurement of the time-varying change in the amount of blood in the tissue volume. In various embodiments, examples of the biological parameter, the physiological parameter, the diagnostic parameter, the pathological parameter or a combination thereof include those which are indicative or a certain condition of the tissue, a condition of the subject or a combination thereof (e.g., atherosclerosis, oxygenation, cardiac output).

In various other embodiments, the method may exclude correlating the measurement of the time-varying change in the amount of blood in the tissue volume to a physiological parameter, a diagnostic parameter, or a pathological parameter.

In accordance with another aspect of the invention, there is provided an apparatus for measuring the time-varying change in an amount of blood in the tissue volume. The apparatus comprises means for exciting the fluorescence agent in the blood, means for acquiring the time-varying light intensity signal during the pulsatile flow of the blood through the tissue volume (where the pulsatile flow may be caused, for example, by a heartbeat or by means simulating the heartbeat such as, for example, a blood pump), the pulsatile flow having a diastolic and a systolic phase resembling a conventional photoplethysmogram, and means for processing the acquired time-varying light intensity signal to obtain a measurement of the time-varying change in the amount of blood in the tissue volume. A modified Beer-Lambert law is applied at the diastolic and systolic phases to obtain:

$$\Delta L = \ln[(I_e\Phi - I_m/I_e\Phi - I_p)](\varepsilon C)^{-1}$$

as was described in connection with the method embodiments.

In various embodiments of the apparatus, the instantaneous molar concentration of the fluorescence agent, C, is determined by a utilization of a concentration-mediated change, including a monotonic spectral shift, in a fluorescence emission spectrum of the fluorescence agent. In various embodiments, the utilization comprises a selection of first and second spectral bands of fluorescence emission spectrum of the fluorescence agent, an acquisition of first and second intensities of fluorescence emission integrated over wavelengths in the first and second spectral bands respectively, a calculation of a ratio of the first and second intensities, and a derivation of a value for C from the ratio.

According to an embodiment, the selection of the first and second spectral bands is such that one of the first and second intensities varies monotonically with C, and one of the first and second intensities is unchanged with C. According to another embodiment, the first and second intensities increase monotonically at different rates with C. According to yet another embodiment, the first intensity increases monotonically with C, and the second intensity decreases monotonically with C. Examples relating to these embodiments are illustrated in FIGS. 3 to 5. In various embodiments, the first spectral band comprises wavelengths ranging from about 780 nm to about 835 nm, or a subset thereof, and the second spectral band comprises wavelengths ranging from about 835 nm to about 1000 nm, or a subset thereof.

Figure 6:
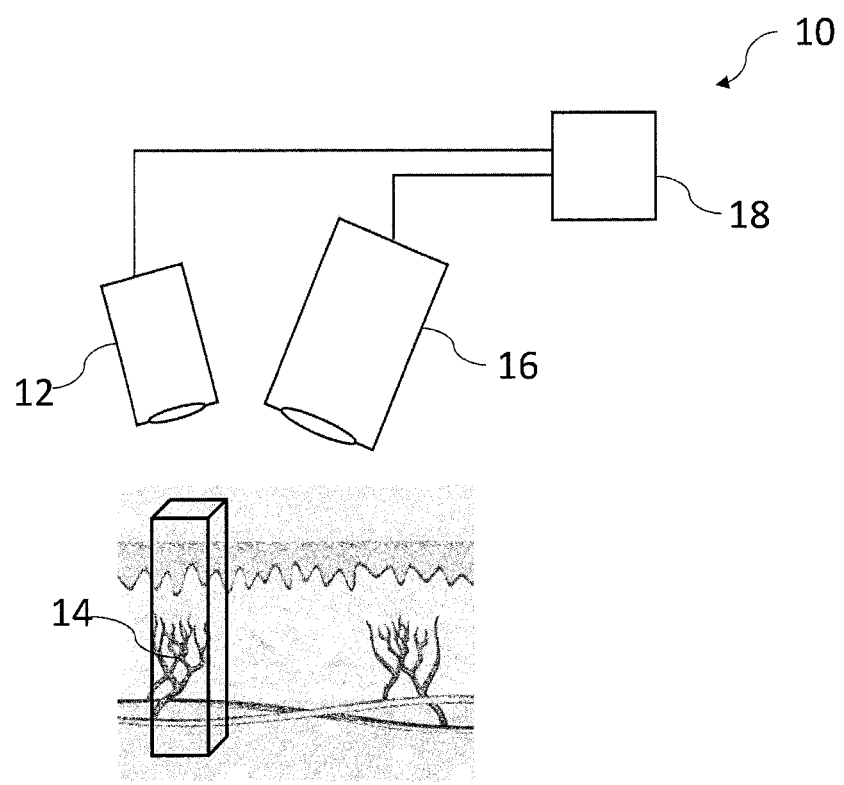
FIG. 6 illustrates an example apparatus for measuring a time-varying change in an amount of blood in a tissue volume according to an embodiment.

Referring to FIG. 6, there is shown schematically an example embodiment of an apparatus 10 for measuring the time-varying change in the amount of blood in the tissue volume. The apparatus 10 comprises means for exciting 12 the fluorescence agent 14 in the blood in the tissue volume, means for acquiring 16 the time-varying light intensity signal during the pulsatile flow of the blood through the tissue volume, and means for processing 18 the acquired time-varying light intensity signal to provide the measurement of the time-varying change in the amount of blood in the tissue volume.

Figure 7:
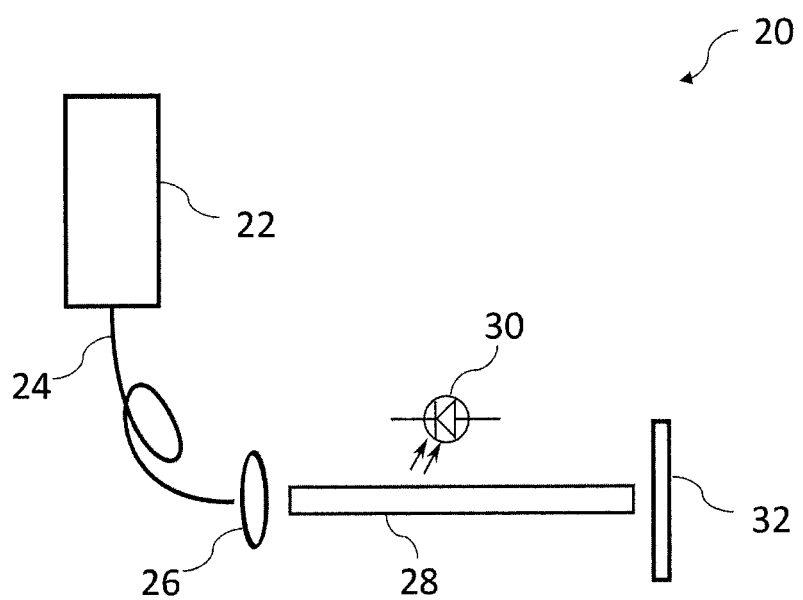
FIG. 7 illustrates an example illumination module according to an embodiment.

In various embodiments, the means for exciting 12 comprises, for example, an illumination module comprising a fluorescence excitation source operatively configured to generate an excitation light having a suitable intensity and a suitable wavelength for exciting the fluorescence agent 14. FIG. 7 shows an example illumination module 20 according to an embodiment. The illumination module 20 comprises a laser diode 22 (e.g., which may comprise, for example, one or more fiber-coupled diode lasers) for providing an excitation light for exciting the fluorescence agent 14 (not shown). Examples of other sources of the excitation light which may be used in various embodiments include one or more LEDs, arc lamps, or other illuminant technologies of sufficient intensity and appropriate wavelength to excite the fluorescence agent 14 in blood. For example, excitation of the fluorescence agent 14 in blood, wherein the fluorescence agent 14 is a fluorescence dye with near infra-red excitation and emission characteristics, may be performed using one or more 793 nm, conduction-cooled, single bar, fiber-coupled laser diode modules from DILAS Diode Laser Co, Germany.

In various embodiments, the light output from the source of the excitation light may be projected through an optical element (i.e., one or more optical elements) to shape and guide the output being used to illuminate the tissue area of interest. The shaping optics may consist of one or more lenses, light guides, and/or diffractive elements so as to ensure a flat field over substantially the entire field of view of the fluorescence emission acquisition module. In particular embodiments, the fluorescence excitation source is selected to emit at a wavelength close to the absorption maximum of the fluorescence agent 14 (e.g., a fluorescence dye such as ICG). For example, referring to the embodiment of the illumination module 20 in FIG. 7, the output 24 from the laser diode 22 is passed through one or more focusing lenses 26, and then through a homogenizing light pipe 28 such as, for example, light pipes commonly available from Newport Corporation, USA. Finally, the light is passed through an optical diffractive element 32 (i.e., one or more optical diffusers) such as, for example, ground glass diffractive elements also available from Newport Corporation, USA. Power to the laser diode 22 itself is provided by, for example, a high-current laser driver such as those available from Lumina Power Inc. USA. The laser may be operated in a pulsed mode during the image acquisition process. In this embodiment, an optical sensor such as a solid state photodiode 30 is incorporated into the illumination module 20 and samples the illumination intensity produced by the illumination module 20 via scattered or diffuse reflections from the various optical elements. In various embodiments, additional illumination sources may be used to provide guidance when aligning and positioning the module over the area of interest.

Figure 8:
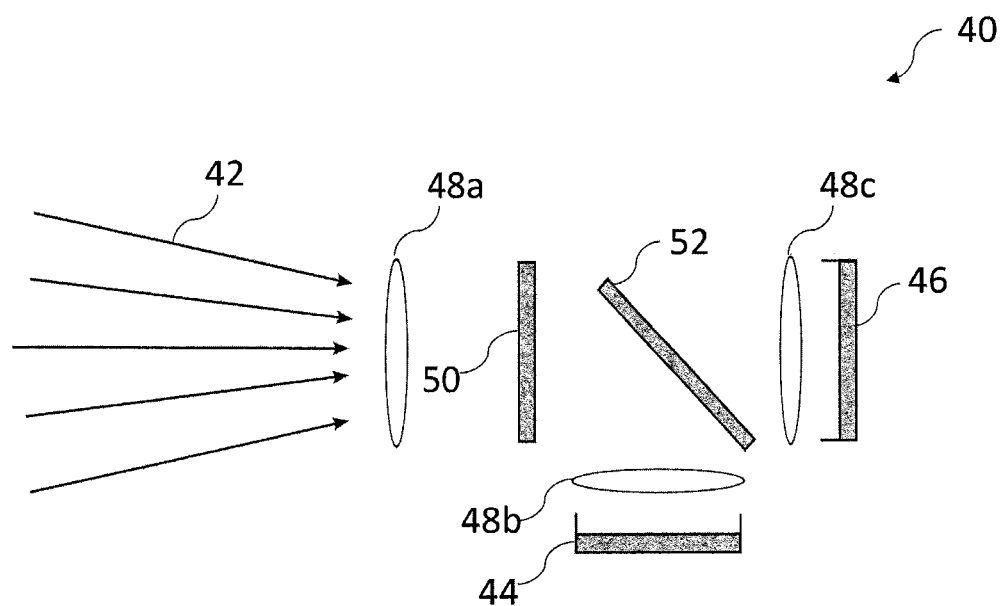
FIG. 8 illustrates an example fluorescence emission acquisition module according to an embodiment.

Referring back to FIG. 6, in various embodiments, the means for acquiring 16 comprises, for example, a fluorescence emission acquisition module for acquiring a fluorescence signal (e.g., the time-varying light intensity signal) from the fluorescence agent 14, the fluorescence emission acquisition module comprising an image sensor. Referring to FIG. 8, there is shown an exemplary embodiment of a fluorescence emission acquisition module 40 for acquiring the fluorescence signal such as the time-varying light intensity signal from the fluorescence agent 14 (not shown). As is shown in FIG. 8, the fluorescence emission 42 from the fluorescence agent 14 in blood (not shown) is collected and focused onto a 2D solid state image sensor (e.g. an image sensor 44 and an image sensor 46) using a system of imaging optics 48a, 48b and 48c. The solid state image sensor may be a charge coupled device (CCD), a CMOS sensor, a CID or similar 2D sensor technology. An optical filter 50 (which may comprise a plurality of optical filters in various arrangements) is used to remove residual and reflected excitation light and to ensure that only the fluorescence emission is recorded at the image sensors 44 and 46. In this embodiment, a dichroic optical filter 52 is used to divide the fluorescence emission spectrum of the fluorescence agent 14 into two spectral channels (e.g., first and second spectral bands). In this embodiment, the dichroic optical filter 52 is designed such that the total fluorescence emission is divided generally equally between the two spectral channels, and such that the shorter wavelength channel collects light of wavelengths equal to or shorter than the fluorescence emission maximum, and the longer wavelength channel collects light equal to or longer than the fluorescence emission maximum. The charge that results from the optical signal transduced by the image sensors 44 and 46 is converted to an electrical video signal, which includes both digital and analog video signals, by the appropriate read-out and amplification electronics in the fluorescence emission acquisition module 40.

Figure 9:
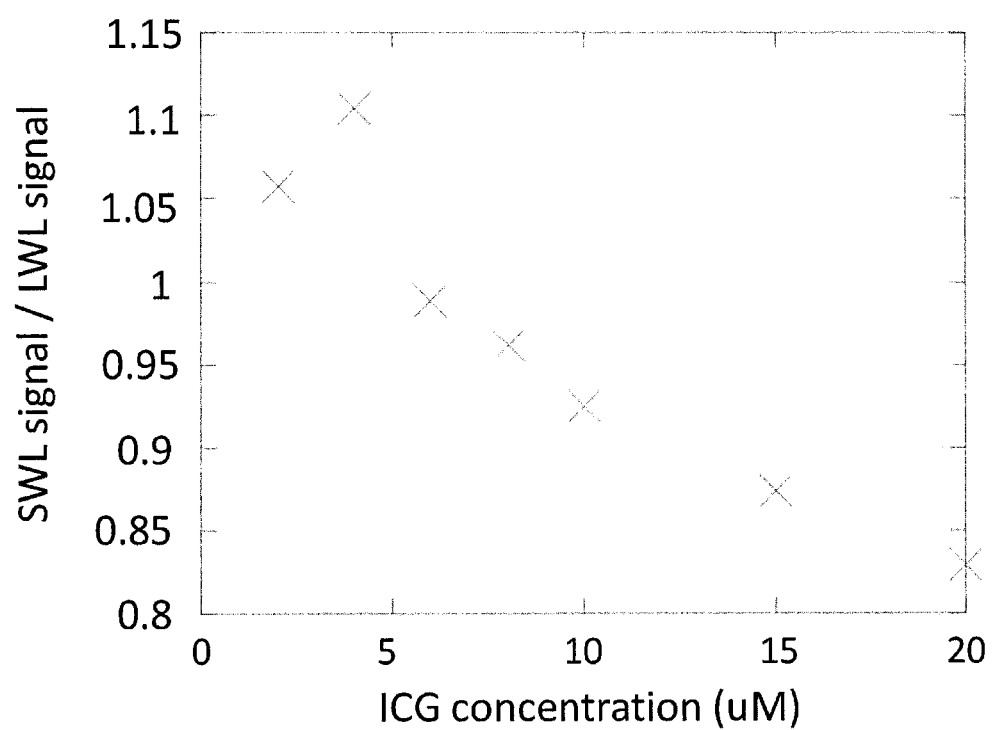
FIG. 9 illustrates an example relationship between a ratio of ICG fluorescence intensities from a first spectral band ranging from about 820 to about 840 nm (where "SWL" denotes a short wavelength) and from the second spectral band ranging from about 840 nm to about 900 nm (where "LWL" denotes a long wavelength) and the instantaneous molar concentration of ICG.

Although only two image sensors 44 and 46 are utilized in the embodiment shown in FIG. 8, the preferred selection of the two spectral bands—where the fluorescence emission over wavelengths in one band monotonically increases with the fluorescence agent concentration and where the fluorescence emission integrated over wavelengths in another band monotonically decreases with the fluorescence agent concentration as shown in FIG. 5—enables the possibility of utilizing the signals transduced by the two sensors in two beneficial ways. Firstly the signal from the two image sensors 44 and 46 may be combined to obtain the total fluorescence image signal intensity. This will enable the highest quality (lowest noise) fluorescent image to be generated. Secondly, the image signal from these two spectral bands can be ratioed on a pixel by pixel basis to determine the instantaneous molar concentration of fluorescence agent 14 in the blood. The molar concentration is an essential parameter in determining the time-varying change in the amount of blood in the tissue volume. The images from the two image sensors 44 and 46 show identical fields of view on a pixel by pixel basis. Furthermore, the range of variation of the ratio as shown in FIG. 9, is increased and the determination of the instantaneous concentration of the fluorescence agent 14 is consequently more accurate by utilizing the selection of the spectral bands as is described in connection with the various embodiments.

Referring back to FIG. 6, in various embodiments, the means for processing 18 comprises, for example, a processor module (not shown) for analyzing time-varying light intensity signals, performing calculations for the plethesmographic computation of the time-varying change in the amount of blood in the tissue volume, outputting the calculated information to an appropriate display and/or recording device, or a combination thereof. In various embodiments, the processor module comprises any computer or computing means such as, for example, a tablet, laptop, desktop, networked computer, or dedicated standalone microprocessor. Inputs are taken, for example, from the image sensors 44, 46 of the emission acquisition module 40 shown in FIG. 8, from the solid state photodiode 30 in the illumination module 20 in FIG. 7, and from any external control hardware such as a footswitch or remote-control. Output is provided to the laser diode driver, and optical alignment aids. In various embodiments, the processor module may have the capability to save image sequences to internal memory, such as a hard disk or flash memory, so as to enable post-processing of acquired data. In various embodiments, the processor module may have an internal clock to enable control of the various elements and ensure correct timing of illumination and sensor shutters. In various other embodiments, the processor module may also provide user input and graphical display of outputs.

Figure 10:
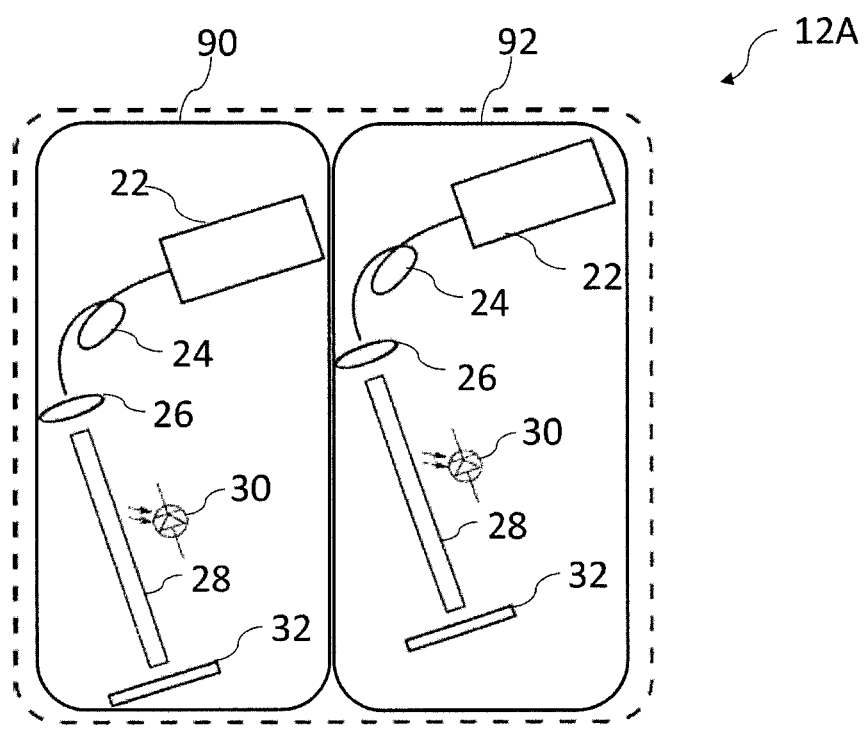
FIG. 10 illustrates an alternative embodiment of the means for exciting for fluorescence excitation of the fluorescence agent of the apparatus in FIG. 6.

In various other embodiments, the apparatus 10 illustrated in FIG. 6, may alternatively comprise the means for exciting 12A for fluorescence excitation of the fluorescence agent 14 (not shown) as illustrated in FIG. 10. The means for exciting 12A comprises an illumination module comprising a first excitation source 90 and a second excitation source 92 for providing an excitation light for exciting the fluorescence agent 14 (not shown). The output from each excitation source is passed through beam shaping and smoothing optics as described in connection with the previous embodiments. In this embodiment, the means for acquiring (not shown) comprises a fluorescence emission acquisition module consisting of fluorescence collecting and imaging optics similar to those described in connection with the previous embodiments, as well as an optical filter for rejection of residual and reflected excitation light (not shown). This system of optics preferably focuses the collected fluorescence onto a single solid-state image sensor, which is read out by the processing module at each frame.

In operation, and with continuing reference to the embodiments in FIGS. 6 to 8, the subject is positioned such that an area of interest is located beneath both the means for exciting 12 comprising the illumination module 20 and the means for acquiring 16 comprising the fluorescence emission acquisition module 40 of the apparatus 10, and such that the illumination module 20 produces a substantially uniform field of illumination across substantially the entire area of interest. In various embodiments, prior to the administration of the fluorescence agent 14 to the subject, an image may be acquired of the area of interest for the purposes of background deduction. For example, in order to do this, the operator may initiate the image acquisition procedure by depressing a remote switch or foot-control, or via a keyboard on the processing module (not shown) of the processing means 18 of the apparatus 10 in FIG. 6. As a result, the excitation source (e.g., the laser diode 22 of the illumination module 20 in FIG. 7) is turned on and begins the shutter sequence for the image sensors (e.g., image sensors 44, 46 of the fluorescence emission acquisition module 40 in FIG. 8). When operating in the pulsed mode of the embodiment, each of the image sensors is read out simultaneously with the laser pulses. In this way, maximum fluorescence emission intensity is recorded, and signal-to-noise ratio is optimized. In this embodiment, the fluorescence agent 14 is administered to the subject and delivered to the area of interest via arterial flow. Image acquisition is initiated, for example, shortly after administration of the fluorescence agent 14, and images of the fluorescence returned from substantially the entire area of interest are acquired throughout the ingress of the fluorescence agent 14. The fluorescence emission from the area of interest is collected by the front imaging optics of the fluorescence emission acquisition module 40. Residual and reflected excitation light is attenuated by the optical filters (e.g., optical filter 50 in FIG. 8).

In the embodiment in FIG. 8, the dichroic optical filter 52 is used to divide the total fluorescence acquired into two selected spectral channels, as is described in connection with the various embodiments. In a single exposure, the images recorded by each sensor 44 and 46 are read out and sent to the processor module (not shown) of the processing means 18 of the apparatus 10 shown in FIG. 6. In various embodiments, the processor module may perform averaging over adjacent pixels in each frame, as well as over multiple successive frames prior to performing any calculations of perfusion. The images recorded in each of the two spectral channels are compared, and the ratio of fluorescence intensity in each channel is calculated over a kernel of the field of view. The kernel may be a single pixel or an array of pixels in the field of view. Based on the calculated ratio, and on a previous calibration of the apparatus, the concentration of ICG within the kernel is calculated. The combined signal from both image sensors 44 and 46 is then used, together with a measurement of the optical illumination intensity as measured by the sampling solid state photodiode 32 within the illumination module 20 in FIG. 7 to calculate the total fluorescence intensity, and determine the volume of blood in the kernel via an application of the modified Beer-Lambert law as is described in connection with the various embodiments. This processing is repeated over substantially the entire field of view, and the resulting measurement of perfusion (blood flow) is displayed to the user on demand as, for example, a grayscale or false color image, or stored for later analysis.

In yet further aspects, there is provided a kit for measuring a time-varying change in an amount of blood in a tissue volume, the kit comprising the apparatus as was described above in connection with the various embodiments, and a fluorescence agent such as, for example, ICG as was described above in connection with the various embodiments.

In yet further aspects, there is provided a fluorescence agent for use in a method for measuring a time-varying change in an amount of blood in a tissue volume of a subject, the various aspects of the method being described above.

While the present invention has been illustrated and described in connection with various embodiments shown and described in detail, it is not intended to be limited to the details shown, since various modifications and structural changes may be made without departing in any way from the scope of the present invention. Various modifications of form, arrangement of components, steps, details and order of operations of the embodiments illustrated, as well as other embodiments of the invention may be made without departing in any way from the scope of the present invention, and will be apparent to a person of skill in the art upon reference to this description. It is therefore contemplated that the appended claims will cover such modifications and embodiments as they fall within the true scope of the invention. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

The invention claimed is:

1. An apparatus for measuring a time-varying change in an amount of blood in a tissue volume, the apparatus comprising:
    an excitation light source configured to excite a fluorescence agent in the blood;
    a light intensity sensor configured to acquire a time-varying light intensity signal during a pulsatile flow of the blood through the tissue volume, the pulsatile flow having a diastolic and a systolic phase; and
    one or more processors configured to process the acquired time-varying light intensity signal to obtain a measurement of the time-varying change in the amount of blood in the tissue volume, wherein a modified Beer-Lambert law is applied at the diastolic and systolic phases to obtain:

$$\Delta L = \ln[(I_e \Phi - I_m / I_e \Phi - I_p)](\varepsilon C)^{-1}$$

where:
$\Delta L$ is a change in aggregate blood layer thickness within a given tissue volume,
$I_e$ is an intensity of an excitation light exciting the fluorescence agent in the blood,
$\Phi$ is a quantum efficiency of the fluorescence agent,
$I_m$ is an intensity of the time-varying light intensity signal during the diastolic phase minimum of the pulsatile flow of the blood through the tissue volume,
$I_p$ is an intensity of the time-varying light intensity signal during the systolic phase maximum of the pulsatile flow of the blood through the tissue volume,
$\varepsilon$ is a molar absorption coefficient for the fluorescence agent,
C is an instantaneous molar concentration of the fluorescence agent in the blood.

2. The apparatus of claim 1 wherein the means for exciting comprises an illumination module comprising a fluorescence excitation source, the fluorescence excitation source operatively configured to generate an excitation light having a suitable intensity and a suitable wavelength for exciting the fluorescence agent.

3. The apparatus of claim 2 wherein the fluorescence excitation source comprises a first excitation source and a second excitation source.

4. The apparatus of claim 2 wherein the illumination module further comprises an optical element operatively configured to shape and guide the excitation light exiting the illumination module to provide a uniform field of the excitation light across an area of interest comprising the tissue volume of the subject.

5. The apparatus of claim 4 wherein the optical element comprises a lens, a light guide, a diffractive element, or a combination thereof.

6. The apparatus of claim 1 wherein the means for acquiring comprises a fluorescence emission acquisition module comprising an image sensor.

7. The apparatus of claim 6 wherein the fluorescence emission acquisition module further comprises an optical element disposed in front of the image sensor operatively configured to capture, filter, and direct the time-varying light intensity signal produced by the fluorescence agent to the image sensor.

8. The apparatus of claim 1 wherein the means for processing comprises a processor module, the processor module being operatively configured to control an operation of the means for causing the fluorescence agent to produce the time-varying light intensity signal, to control an operation of the means for acquiring the time-varying light intensity signal, or a combination thereof.

9. A kit for measuring a time-varying change in an amount of blood in a tissue volume, the kit including the apparatus of claim 1 and a fluorescence agent.

10. A method for measuring a time-varying change in an amount of blood in a tissue volume, the method performed at an apparatus comprising an excitation light source, a light intensity sensor, and one or more processors, the method comprising:
    exciting, by the excitation light source, a fluorescence agent in the blood;
    acquiring, by the light intensity sensor, a time-varying light intensity signal during a pulsatile flow of the blood through the tissue volume, the pulsatile flow having a diastolic and a systolic phase; and
    processing, by the one or more processors, the acquired time-varying light intensity signal to obtain a measurement of the time-varying change in the amount of blood in the tissue volume, wherein a modified Beer-Lambert law is applied at the diastolic and systolic phases to obtain:

$$\Delta L = \ln[(I_e \Phi - I_m / I_e \Phi - I_p)](\varepsilon C)^{-1}$$

where:
$\Delta L$ is a change in aggregate blood layer thickness within a given tissue volume,
$I_e$ is an intensity of an excitation light exciting the fluorescence agent in the blood,
$\Phi$ is a quantum efficiency of the fluorescence agent,
$I_m$ is an intensity of the time-varying light intensity signal during the diastolic phase minimum of the pulsatile flow of the blood through the tissue volume,
$I_p$ is an intensity of the time-varying light intensity signal during the systolic phase maximum of the pulsatile flow of the blood through the tissue volume,
$\varepsilon$ is a molar absorption coefficient for the fluorescence agent,
C is an instantaneous molar concentration of the fluorescence agent in the blood.

11. The method of claim 10 wherein C is determined by utilizing a concentration-mediated change in a fluorescence emission spectrum of the fluorescence agent.

12. The method of claim 11 wherein the concentration-mediated change includes a spectral shift in the fluorescence emission spectrum of the fluorescence agent.

13. The method of claim 11 wherein the utilizing comprises:
    selecting first and second spectral bands of fluorescence emission spectrum of the fluorescence agent;
    acquiring first and second intensities of fluorescence emission integrated over wavelengths in the first and second spectral bands respectively;

calculating a ratio of the first and second intensities; and
deriving a value for C from the ratio.

14. The method of claim 13 wherein the selection of the first and second spectral bands is such that:
one of the first and second intensities varies monotonically with C, and one of the first and second intensities is unchanged with C;
(ii) the first and second intensities increase monotonically with C but at different rates; or
(iii) the first intensity increases monotonically with C, and the second intensity decreases monotonically with C.

15. The method of claim 13 wherein the first spectral band comprises wavelengths ranging from about 780 nm to about 835 nm, or a subset thereof, and the second spectral band comprises wavelengths ranging from about 835 nm to about 1000 nm, or a subset thereof.

16. The method of claim 10 wherein the fluorescence agent is indocyanine green (ICG).

17. The method of claim 16 wherein C ranges from about 2 µM to about 10 mM.

* * * * *